Figure 1:
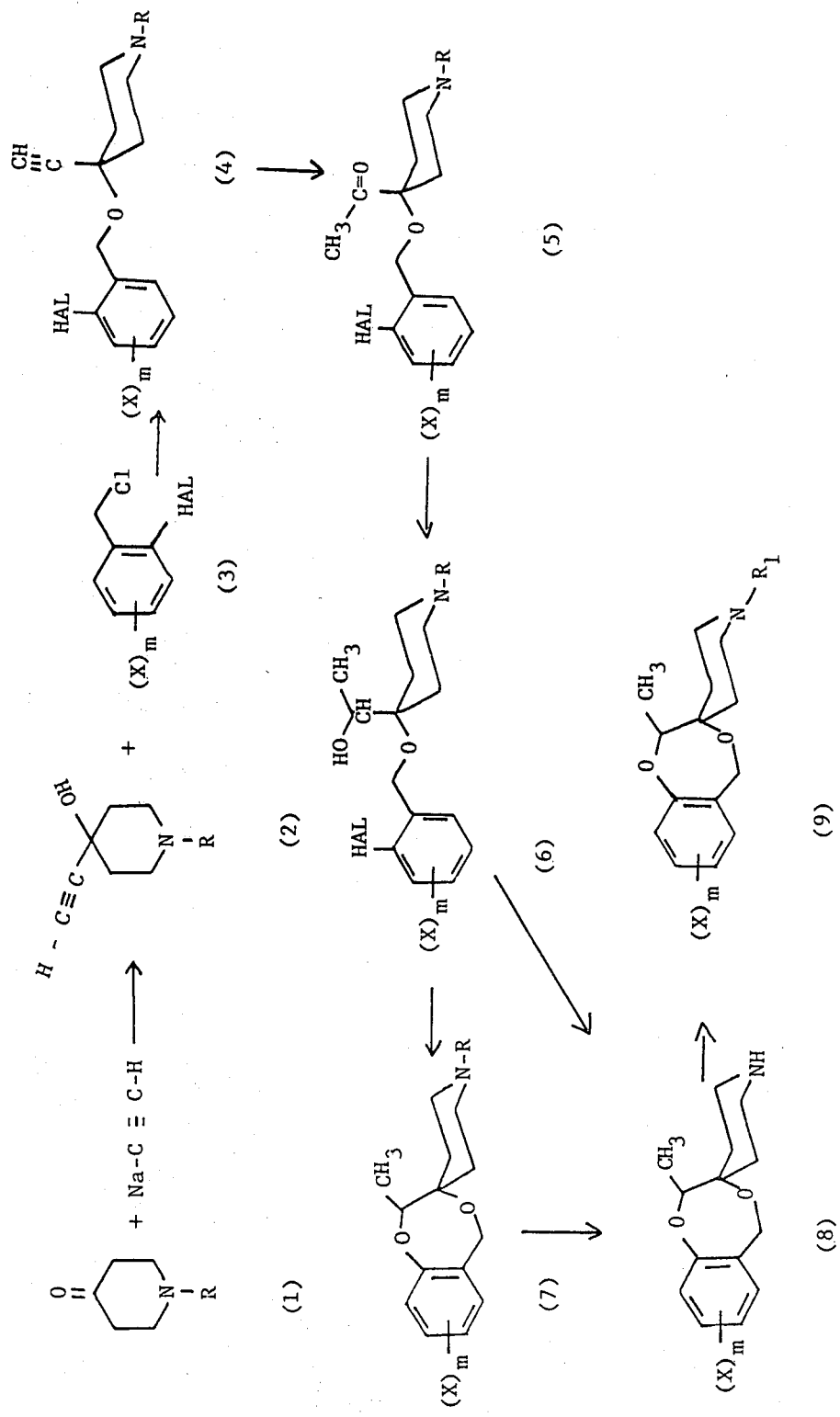

ical Patent [19]                [11]  4,405,631
Kosley, Jr. et al.                   [45]  Sep. 20, 1983

[54] SPIRO[2H-1,4-BENZODIOXEPIN-3(5H)4'-PIPERIDINE AND -3'PYRROLIDINE] COMPOUNDS AND THEIR USE AS ANTIHYPERTENSIVE AGENTS

[75] Inventors: Raymond W. Kosley, Jr., Bridgewater; Robert J. Cherill, Somerset, both of N.J.

[73] Assignee: Hoechst-Roussel Pharmaceuticals Inc., Somerville, N.J.

[21] Appl. No.: 410,155

[22] Filed: Aug. 20, 1982

[51] Int. Cl.³ ............... C07D 491/113; A61K 31/455
[52] U.S. Cl. .................................. 424/267; 124/274; 546/17; 546/216; 546/221; 546/208
[58] Field of Search ......................... 546/17; 548/409; 424/267, 274

[56]         References Cited
        FOREIGN PATENT DOCUMENTS
    469736  4/1969  Switzerland ...................... 546/17

Primary Examiner—Robert T. Bond

[57]            ABSTRACT

Spiro[2H-1,4-benzodioxepin-3(5H)4'-piperidine and -3-pyrrolidine] compounds of the formula where the substituents are as defined herein, are useful in the treatment of hypertension in mammals. Such compounds, their use as antihypertensive agents, pharmaceutical compositions containing the compounds, intermediates and processes for preparing the compounds are provided.

55 Claims, 2 Drawing Figures

FIG. I

SPIRO[2H-1,4-BENZODIOXEPIN-3(5H)4'-PIPERIDINE AND -3'PYRROLIDINE] COMPOUNDS AND THEIR USE AS ANTIHYPERTENSIVE AGENTS

This invention relates to spiro[2H-1,4-benzodioxepin-3(5H)4'-piperidine and -3'-pyrrolidine] compounds. The compounds are useful in the treatment of hypertension in mammals.

Hypertension in mammals may accompany many disorders, such as renal disease, disease of the adrenal gland and toxemia of pregnancy. In most patients with high blood pressure, however, no primary disorder is evident and the condition is referred to as essential hypertension.

In controlled trials with patients afflicted with hypertension, it has been found that hypertensive patients have more frequent cerebral and other cardiovascular accidents than those whose blood pressure has been lowered by drugs. In addition, although hypertension may exist without inducing symptoms in the patient, it is more usual that clinical manifestations develop after elevated blood pressure has persisted for some time. For example, hypertension has been associated with secondary effects, such as headache, dizziness, nose-bleeding, breathlessness on exertion, heart failure and stroke. Since these secondary effects may present a danger to life, it is desirable to lower the blood pressure and maintain it at a more nearly normal level.

A variety of antihypertensive drugs have been introduced for the treatment of elevated blood pressure. Their development has represented an important advance in modern medicine. Intensive efforts are being made to develop new types of antihypertensive drugs and the need for such drugs continues.

This invention aids in fulfilling this need in the art by providing compounds of the formula

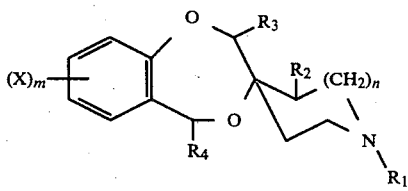

wherein $R_1$ is a $C_3$ or $C_4$ branched or straight chain alkyl or alkenyl group or a $C_4$-alkynyl group terminally substituted by one or two substituents independently selected from the group consisting of

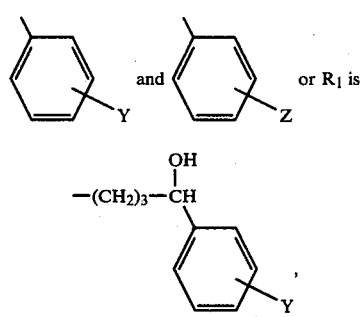

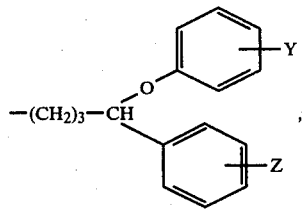

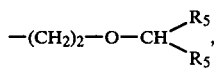

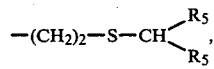

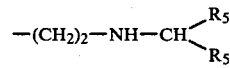

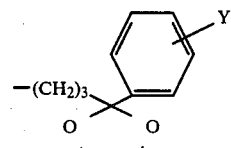

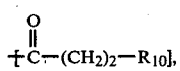

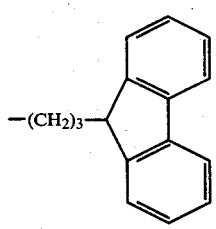

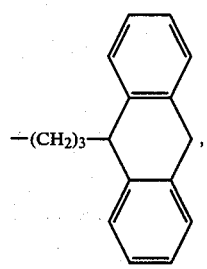

where
Y and Z are the same or different and are independently selected from the group consisting of H, Cl, F, Br, I, —$NO_2$, —$CF_3$, $C_1$ to $C_4$ straight chain alkyl, alkoxy containing $C_1$ to $C_4$ straight chain alkyl, acyl or —$NH_2$;

each $R_5$ substituent is independently selected from the group consisting of

$R_{10}$ is 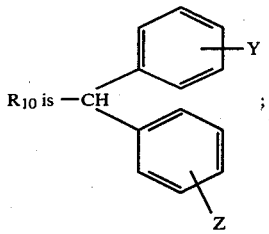 ;

$R_2$ is hydrogen when $n=0$ or $R_2$ is hydrogen or a $C_1$ to $C_3$ straight chain alkyl group when $n=1$;

$R_3$ is hydrogen or a $C_1$ to $C_3$ straight chain alkyl group;

$R_4$ is hydrogen or a $C_1$ to $C_3$ straight chain alkyl group;

m is zero, 1 or 2;

X is Cl, F, Br, I, $-NO_2$, $-CF_3$, $-NR_6R_7$,

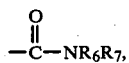

$C_1$ to $C_6$ branched or straight chain alkyl, $-CN$, $-O-R_6$, $-SR_7$, $-SO_3R_7$,

$-NHCOR_8$, $-SO_2R_9$ or $-SOR_9$ where $R_6$ is hydrogen or a $C_1$ to $C_6$ straight chain alkyl group, $R_7$ is hydrogen or a $C_1$ to $C_6$ straight chain alkyl group, $R_8$ is a $C_1$ to $C_6$ branched or straight chain alkyl group, $R_9$ is a $C_1$ to $C_6$ straight chain alkyl group;

provided that when $m=2$, the X-substituents can be the same only when X is selected from the group consisting of H, Cl, F, Br, I, $C_1$ to $C_6$ branched or straight chain alkyl or $-O-R_6$;

n is zero or 1;

and the pharmaceutically acceptable salts thereof.

It is to be understood that when $R_1$ is a $C_4$-alkynyl group, the acetylenic bond is between carbon atom numbers 2 and 3 of the group, i.e., $-CH_2-C\equiv C-CH<$.

In the preferred embodiment of this invention, the compounds of the invention are represented by the following formula

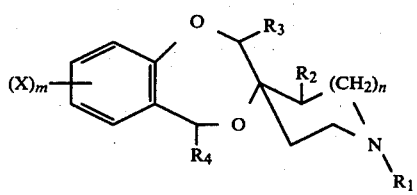

wherein $R_1$ is a $C_4$ branched or straight chain alkyl or alkenyl group terminally substituted by p-fluorophenyl, bis-phenyl or bis-p-fluorophenyl groups; or $R_1$ is

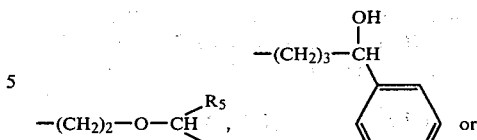

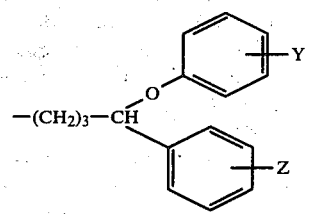

where $R_2$, $R_3$ and $R_4$ are independently selected from hydrogen and $-CH_3$;

X is H, Cl, F, Br, I, $-NO_2$, $-CH_3$ or

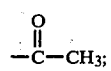

$R_5$, Y and Z are defined above;

m is zero, 1 or 2;

n is zero or 1;

provided that, when $m=2$, the X-substituents can be the same only when X is selected from the group consisting of H, Cl, F, Br, I, $-CH_3$ and $-OCH_3$ and the pharmaceutically acceptable salts thereof.

The particularly preferred compounds of this invention can be represented by the formula

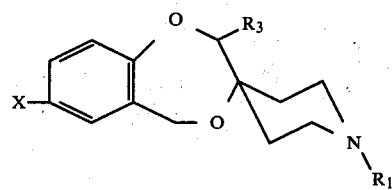

wherein $R_1$ is 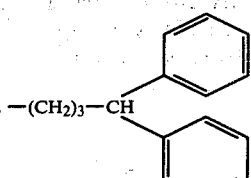 , and X = Cl, F, or Br;

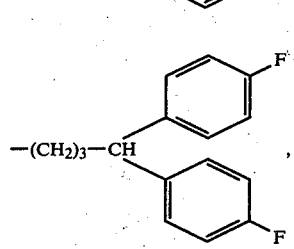

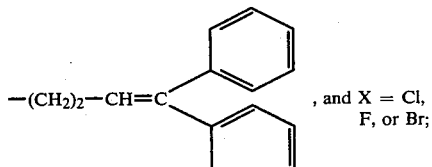, and X = Cl, F, or Br;

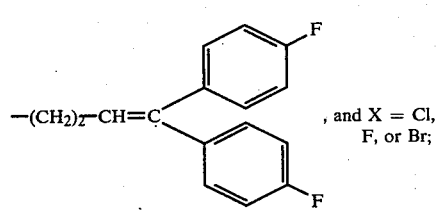, and X = Cl, F, or Br;

R₃ is H or —CH₃;
X is H, Cl, F or Br;
and the pharmaceutically acceptable salts thereof.

These compounds are particularly preferred because of their relative ease of manufacture and because they exhibit relatively high antihypertensive activity in laboratory tests on animals.

This invention also provides compounds of the following formulae, which are useful intermediates in the preparation of the pharmaceutically active compounds of the invention:

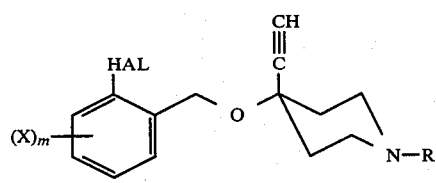 (4)

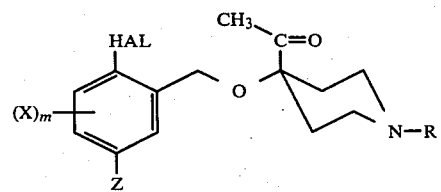 (5)

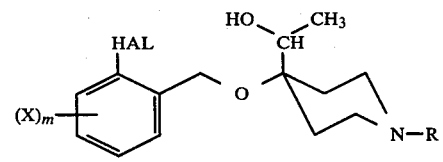 (6)

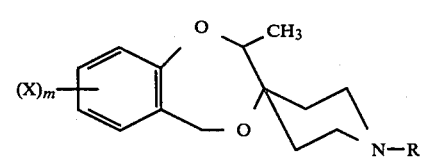 (7)

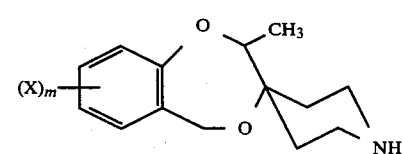 (8)

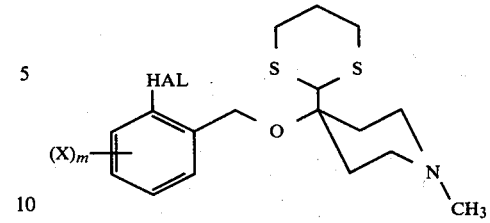 (14)

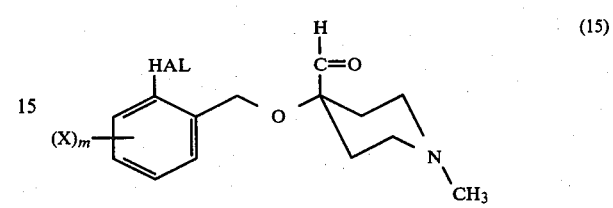 (15)

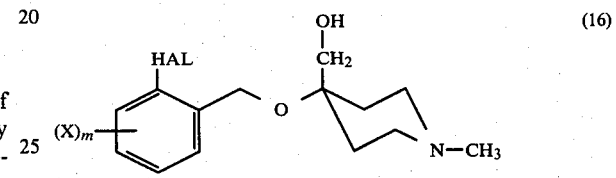 (16)

(—CH₃) (17)

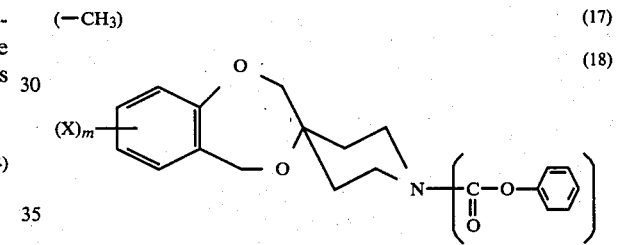 (18)

(—H) (19)

where X and m are as previously defined;
R is hydrogen or a methyl, acyl or benzyl group; and
HAL is chlorine or fluorine.

This invention also provides processes for preparing the compounds of this invention.

Further, this invention provides a method of alleviating hypertension in a mammal by administering to a mammal a pharmaceutically active compound of the invention in an amount sufficient to reduce the blood pressure of the mammal.

Finally, this invention provides a pharmaceutical composition comprising a pharmaceutically active compound of the invention and a pharmaceutically acceptable carrier therefor.

The preparation of the compounds of this invention will now be explained with reference to the Figures, which are schematic diagrams depicting various routes of synthesis of piperidine derivatives of the invention. It will be understood that similar techniques can be employed to synthesize the pyrrolidine derivatives of the invention.

Referring to FIG. 1, the starting reactant is an N-substituted-4-piperidone of formula (1), which is commercially available or can be prepared using well-known techniques for synthesizing organic compounds. The substituent R shown in this Figure can typically be a methyl, acyl or benzyl group. The piperidone of formula (1) can be reacted in tetrahydrofuran (THF) with an ammonical solution of sodium acetylide to obtain a 1-substituted-4-ethynyl-4-piperidinol of formula (2). The resulting 1-substituted-4-ethynyl-piperidinol can be reacted with a substituted or unsubstituted o-halobenzylchloride of formula (3) in solution in the presence of a base, such as potassium t-butoxide or sodium hydride, to yield a 1-substituted-4-ethynyl-4-(o-halobenzyloxy)-piperidine of formula (4). Substituted and unsubstituted compounds of formula (3) are also readily available or can be prepared using conventional techniques. The halo group in the compounds of formula (3) is identified in FIG. 1 as HAL and is chlorine or fluorine, the latter being preferred.

Hydrolysis converts the ethynyl group in the compound of formula (4) to an oxoethyl group. This is achieved by reacting the compound of formula (4) with water catalyzed by mercuric sulphate in an acidic medium, such as methanol/sulphuric acid. The resulting 4-(1-oxoethyl)-4-(o-halobenzyloxy)-piperidine of formula (5) is isolated. If the substituent R in the compound of formula (4) is an acyl group, this group is hydrolyzed so that R is hydrogen in the compound of formula (5).

The keto group of the compound of formula (5) is reduced to a hydroxyl group in solution by sodium borohydride, for example, to form a 4-(1-hydroxyethyl)-4-(o-halobenzyloxy)-piperidine of formula (6).

The alcohol of formula (6) can be cyclized to form the dioxepin ring system of the compounds of the invention. The cyclization can be carried out in the presence of a base, such as potassium t-butoxide or sodium hydride, in a solvent, such as dimethyl sulfoxide (DMSO) or THF, at temperatures from room temperature to reflux temperature. If the substituent R in the alcohol of formula (6) is hydrogen, then the compound of formula (8) in FIG. 1 will be obtained. If the substituent R is a methyl, acyl or benzyl group, then the cyclization reaction will produce a compound of formula (7).

The compound of formula (8) can be obtained from the compound of formula (7) by removing the methyl, acyl or benzyl group using conventional techniques. For example, if R is methyl, the compound of formula (7) can be converted to a carbamate, such as by reaction with ethyl chloroformate, followed by hydrolysis with a base, such as potassium hydroxide. The same technique can be employed if R is a benzyl group. Alternatively, the benzyl group can be removed by catalytic hydrogenation, such as by use of a palladium on carbon catalyst. If the substituent R is an acyl group, the acyl group will usually be removed during the formation of the compound of formula (5), but similar hydrolysis of the compound of formula (7) will yield the compound of formula (8).

The substituent $R_1$ can be introduced into the compounds by alkylation of the piperidine nitrogen of the compound of formula (8) with substituted alkyl, alkenyl or alkynyl halides or sulfonate esters to obtain a compound of formula (9). The reaction can be carried out in an aprotic solvent, such as N,N-dimethylformamide (DMF) or n-butyl acetate. The reaction is carried out in the presence of an acid scavenger, such as potassium carbonate or sodium carbonate. Sodium bicarbonate can be employed with some base sensitive materials or olefins. A catalyst, such as potassium iodide, can also be employed. The reaction is typically carried out at a temperature from about ambient to about 125° C., preferably about 20° C. to about 90° C. Typically, the reaction time will be about 45 minutes to about 18 hours. While the reactants can be employed in equimolar amounts, the alkyl, alkenyl or alkynyl halide is often used in excess amount. Generally, the alkyl, alkenyl and alkynyl halides will not exceed about 10% molar excess of the compound of formula (8). If the $R_1$ substituent contains an olefinic group, it may be necessary to add alkylating agent to the reaction medium to replace portions of the agent that may undergo side reactions. The alkylating reaction can be carried out in air or under inert gas, such as a nitrogen blanket. It is preferable to mildly agitate the reaction mixture during the course of the reaction. The alkylating agents employed in this invention are either commercially available or can be prepared by conventional techniques.

In some cases it is necessary to subject the piperidine of formula (9) to further processing to obtain the desired $R_1$-substituent. For example, compounds of the invention in which $R_1$ is

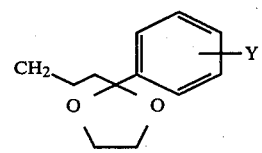

where Y is as previously defined, can be prepared by alkylation of the free base of formula (8) as previously described. The resulting compound can then be reacted with acidified aqueous alcohol solution at elevated temperature to form a piperidine of the invention in which $R_1$ is

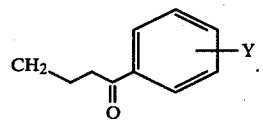

Treatment of the keto group in substituent $R_1$ with a reducing agent, such as sodium borohydride, in solution results in the formation of compounds of the invention in which $R_1$ is

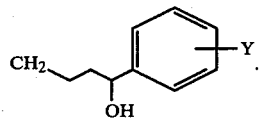

The resulting hydroxyl-containing substituent can be converted to an ether-containing substituent of the formula

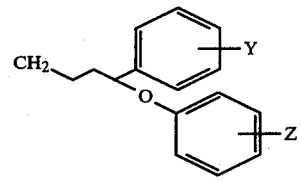

where Y and Z are previously defined, by formation of an anion with, for example, sodium hydride, and then reaction with an aryl halide, for example, 1,4-difluorobenzene.

Once the compounds of formula (7) or (8) are obtained, substituent —X can often be readily introduced into the compounds using conventional techniques. Addition of substituent —X to the benzodioxepin ring system is facilitated by the presence of the oxygen in the 1-position of the dioxepin ring, which functions as an ortho/para-directing substituent. As an example of a reaction for introducing substituent —X into the compounds of the invention, a salt of the compound of formula (7) or (8) can be reacted with N-chlorosuccinimide or N-bromosuccinimide in solution. A compound of formula (7) or (8) in which the substituent —X is chlorine or bromine, respectively, will be obtained. Other similarly well-known reactions can be employed to introduce other species of the X-substituent into the compounds.

When the substituent $R_2$ is other than hydrogen the $R_2$ substituent is conveniently introduced into the compounds of the invention during an early stage of preparation. For example, $R_2$ can be substituted onto the piperidone of formula (1) by alkylation via an enamine. Thus, the piperidone can be converted to enamine, which can be alkylated. Other standard methods, such as formation of a hydrazone followed by alkylation and hydrolysis to form a ketone, can also be employed.

Compounds of the invention in which $R_4$ is other than hydrogen can also be prepared by introducing the $R_4$ substituent at an early stage of the synthesis. For instance, the substituent $R_4$ can be introduced as part of the compound of formula (3). Instead of the benzyl chloride (3), a compound of the formula

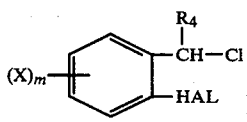

can be utilized where X, m, HAL and $R_4$ are as previously defined. Compounds of this type can be readily prepared using conventional techniques.

Figure 2:
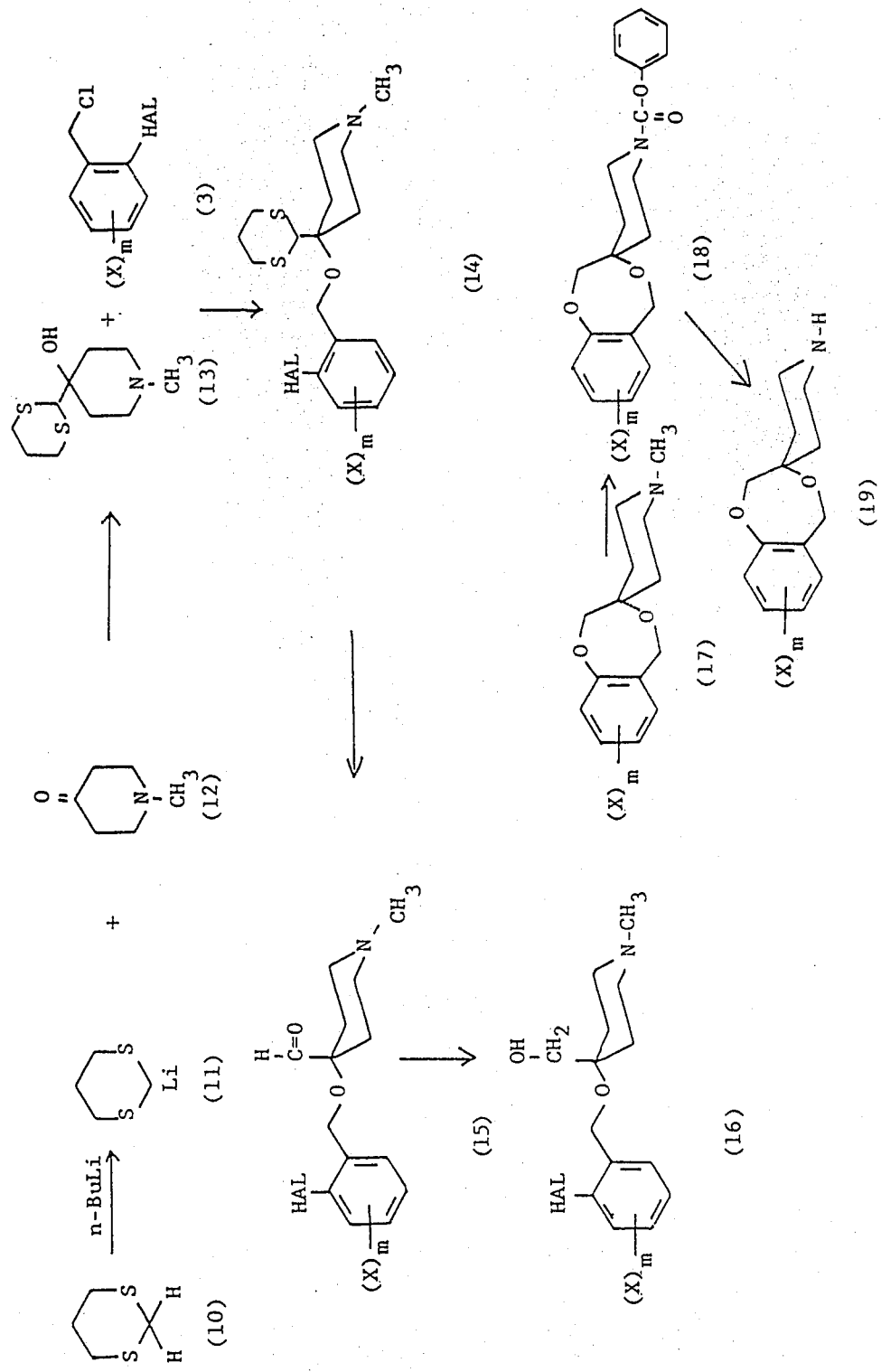

When the substituent $R_3$ is other than hydrogen or —$CH_3$, the $R_3$ substituent is conveniently introduced into the compounds of the invention at an intermediate stage of the synthesis. For example, addition of a Grignard reagent to the aldehyde of formula (15) in FIG. 2 and hydrolysis of the resulting intermediate will form an alcohol analogous to the compound of formula (6). The aldehyde of formula (15) can be synthesized as shown or by other methods known in the art. In addition, other well-known methods for adding alkyl groups to aldehydes and ketones can be employed.

It will be apparent from FIG. 1 that the reaction sequence depicted results in the preparation of compounds of the invention in which the substituent $R_3$ is a methyl group. Corresponding compounds in which $R_3$ is hydrogen can be prepared according to the general reaction scheme depicted in FIG. 2. In this case, 1,3-dithiane of formula (1) is reacted with n-butyllithium to form a lithium salt of formula (11). The lithium salt is then reacted with a commercially available methyl-substituted 4-piperidone of formula (12) in solution in a solvent, such as tetrahydrofuran, to form the alcohol of formula (13). The alcohol (13) is reacted with a substituted or unsubstituted o-halobenzylchloride of formula (3) as previously described. This reaction can be carried out in a solvent, such as tetrahydrofuran, in the presence of a base, such as potassium t-butoxide, to form the compound of formula (14). The ketone of formula (15) is formed by reacting the compound of formula (14) with mercuric oxide in the presence of boron trifluoride in solution. The alcohol of formula (16) is prepared from the ketone (15) using the technique described in connection with the preparation of the alcohol of formula (6) in FIG. 1.

The alcohol of formula (16) can then be cyclized as previously described to form the compound of formula (17). If the tertiary amino group is converted to a secondary amino group, compounds of the invention containing the substituent $R_1$ can be readily prepared by alkylation of the piperidine nitrogen with substituted alkyl, alkenyl or alkynyl halides or sulfonate esters, as previously described. Conversion to the secondary amino group can be accomplished by reacting the compound of formula (17) with phenylchloroformate to convert the methyl group to a phenoxycarbonyl group as shown in formula (18), which can then be converted to the free base of formula (19) by reaction with aqueous sodium hydroxide in a solvent, such as methanol.

It will be understood that this invention includes the compounds of the invention in all of their stereoisomeric forms, including their enantiomers and diastereomers. This invention also contemplates using mixtures of such forms in the treatment of hypertension in mammals.

It will also be understood that the compounds of the invention and intermediates for their preparation can exist in either the form of a free base or as an acid addition salt. For example, it is often convenient to isolate compounds from reaction mixtures by precipitating them from solution by the addition of an acid having a pharmaceutically acceptable anion. The precipitate can be recovered and purified, and the resulting salt converted to its free base by addition to an alkaline medium.

Compounds of this invention are useful as antihypertensive agents due to their ability to depress blood pressure in mammals. Antihypertensive activity is measured in the spontaneous hypertensive rat by the indirect tail cuff method described by A. Schwartz, Ed., Methods in Pharmacology, Vol. I, page 135, Appleton Century Crafts, New York (1971). In this procedure, a group of five animals is treated orally with the drug for three days in relation to a control group of the same number. The drop in blood pressure is measured on the third day following administration. The antihypertensive activity is expressed as mm Hg decrease in mean arterial blood pressure. Some of the compounds of this invention were tested according to this spontaneous hypertensive rat (SHR) test and were found to produce the results shown in Table I. The dose is indicated as mg of the compound per kg body weight by peroral (PO) administration.

TABLE I

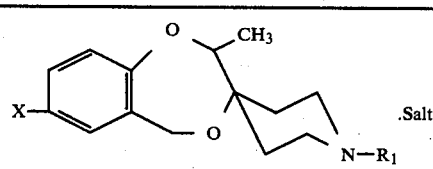

| Compound of Example | Salt | X | $R_1$ | SHR mm Hg | Dose mg/kg PO |
|---|---|---|---|---|---|
| 36 | $C_2H_2O_4$ | H | H | −42 | 50 |

TABLE I-continued

General structure:

X—(2-methylphenyl-CH₂)—O—C(CH₃)(cyclohexane with N—R₁)—O  · Salt

| Compound of Example | Salt | X | R₁ | SHR mm Hg | Dose mg/kg PO |
|---|---|---|---|---|---|
| 8 | C₂H₂O₄ | H | CH₂—CH(4-F-C₆H₄)(4-F-C₆H₄) | −102 | 50 |
| 9 | C₄H₄O₄ | H | CH₂—C(4-F-C₆H₄)(O-CH₂-CH₂-CH₂-O) (cyclic ketal) | −34 | 50 |
| 10 | C₄H₄O₄ | H | CH₂—CH=C(4-F-C₆H₄)(4-F-C₆H₄) | −18 | 50 |
| 11 | C₂H₂O₄ | H | CH₂—CH(C₆H₅)(C₆H₅) | −17 | 50 |
| 12 | C₄H₄O₄ | H | CH₂—CH=C(C₆H₅)(C₆H₅) | −20 | 50 |
| 16 | C₂H₂O₄ | Cl | CH₂—CH=C(C₆H₅)(C₆H₅) | −47 | 50 |
| 17 | C₂H₂O₄ | Cl | CH₂—CH(C₆H₅)(C₆H₅) | −43 / −23 | 50 / 3 |
| 14 | HCl | H | CH₂—CH₂—(4-F-C₆H₄) | −34 | 50 |
| 18 | C₂H₂O₄ | Cl | CH₂—CH(4-F-C₆H₄)(4-F-C₆H₄) | −41 | 0.3 |
| 19 | C₂H₂O₄ | Cl | CH₂—CH=C(4-F-C₆H₄)(4-F-C₆H₄) | −43 | 10 |
| 23 | H |  | CH₂—CH₂—CH(OH)(4-F-C₆H₄) | −31 | 10 |
| 20 | HCl | Cl | CH₂—CH(C₆H₅)(C₆H₅) | −15 | 50 |
| 22 | C₂H₂O₄ | H | CH₂—CH₂—(4-(4-F-C₆H₄-O)-C₆H₄) | −24 | 50 |
| 21 | C₂H₂O₄ | Br | CH₂—CH(4-F-C₆H₄)(4-F-C₆H₄) | −74 / −63 | 50 / 3 |
| 15 | C₂H₂O₄ | H | CH₂—CH(4-Cl-C₆H₄)(4-Cl-C₆H₄) | −27 | 50 |
| 41 | HCl | F | CH₂—CH(C₆H₅)(C₆H₅) | −34 | 50 |
| 42 | HCl | F | CH₂—CH(4-F-C₆H₄)(4-F-C₆H₄) | −126 | 50 |

The above data illustrates that compounds of the present invention are useful for the treatment of hypertension when administered to mammals. Compounds of the invention compare favorably with the well-known drug α-methyl dopa which, in a similar test, gives an SHR value of —40 mm Hg when administered at 50 mg/kg PO for five days.

Typically, the dose of the compounds of the invention will be from about 0.1 to about 50 mg/kg of body weight per day.

The compounds of the present invention may be administered in a pharmaceutically effective amount to a subject by a convenient route, such as orally, intramuscularly, intravenously, subcutaneously or intraperitoneally. The preferred route of administration is oral, for example, with an inert diluent or with an edible carrier or in gelatin, capsules or tablets.

For the purpose of oral therapeutic administration, the active compounds of this invention may be incorporated with excipients and used in the form of tablets, troches, capsules, exilirs, suspensions, syrups, wafers, chewing gum and the like. These preparations should contain at least about 0.5% by weight of active compound, but the amount of active ingredient may be varied depending on the particular form and may typically be between about 7 to about 70% by weight of the unit. The amount of active compound in such compositions is such that a suitable dosage will be obtained. Preferred compositions in preparations according to the present invention are prepared so that an oral dosage unit form contains between about 1 and about 200 mg of active compound.

The tablets, pills, capsules, troches and the like may also contain the following adjuvants; a binder, such as gum tragacanth or gelatin; an excipient, such as starch or lactose; a disintegrating agent, such as algenic acid, potato starch and the like; a lubricant, such as magnesium stearate; a sweetening agent, such as sucrose or saccharine, or a flavoring agent, such as peppermint, methylsalicylate or orange flavoring. When the dosage unit form is a capsule, it may contain in addition to materials of the above type, a liquid carrier, such as a fatty oil. Other dosage unit forms may contain various other materials that modify the physical form of the dosage unit, for example, coatings. Thus, tablets or pills may be coated with sugar, shellac, or both. A syrup may contain, in addition to the active compounds, sucrose as a sweetening agent, preservatives, colorings, and flavors. Materials employed in preparing these various compositions must be pharmaceutically pure and non-toxic in the amounts utilized.

For the purpose of parenteral therapeutic administration, the active compounds of the invention may be incorporated into a solution or suspension. These preparations should contain at least about 0.1% by weight of active compound, but may be varied to typically contain about 0.5 to about 30% of the weight thereof. The amount of active compound in such compositions is such that a suitable dosage will be obtained. Preferred compositions in preparations according to the present invention are prepared so that a parenteral dosage unit contains between about 0.5 to about 100 mg of active compound.

The solutions or suspensions may also include the following components: a sterile diluent, such as water, for injection, saline solution, fixed oils, polyethylene glycols, glycerine, propylene glycol or other synthetic solvents; antibacterial agents, such as benzyl alcohol or methyl paraben; antioxidants, such as ascorbic acid or sodium bisulfite; chelating agents, such as ethtylenediamine tetraacetic acid; buffers, such as acetates, citrates, or phosphates; and agents for the adjustment of tonicity, such as sodium chloride or dextrose. Parenteral preparations can be enclosed in ampules, disposable syringes or multiple dose vials made of glass or plastic.

The compounds of the invention, while effective in themselves, may be formulated and administered in the form of their pharmaceutically acceptable addition salts for purposes of stability, convenience of crystallization, increased solubility and the like. Such salts include the salts of inorganic acids, such as hydrochloric acid, hydrobromic acid, sulfuric acid and nitric acid. Salts of organic acids, such as citric, fumaric, maleic and tartaric acids, can also be employed.

This invention will now be described in greater detail in the following Examples.

EXAMPLE 1

1-Acetyl-4-ethynyl-4-piperidinol

To 350 ml of liquid ammonia was added 0.06 g of ferric nitrate. When the ferric nitrate dissolved, 1.0 g of sodium was added. The mixture was stirred until a black precipitate formed. To the mixture was then added 3.25 g of sodium. The solution was stirred until the mixture turned gray after which acetylene was bubbled through the reaction for 2 hrs. To the mixture was then added 25 g (0.177 mol) of N-acetyl-4-piperidone in 100 ml of dry THF. The mixture was subsequently stirred for 3 hrs. during which time acetylene was bubbled through. The reaction was then quenched by addition of 10 g (0.187 mol) of ammonium chloride. The ammonia was allowed to evaporate overnight. To the mixture was then added 75 ml of saturated ammonium nitrate and 40 ml of 25% ammonium hydroxide. The mixture was then extracted twice with chloroform, dried over potassium carbonate, filtered and the solvent evaporated to provide a white solid. The solid was washed with anhydrous ether and dried. The crude yield of 1-acetyl-4-ethynyl-4-piperidinol was 17.9 g (0.107 mol, 60.6%). Recrystallization from ethyl acetate provided analytically pure material, m.p. 132°–134° C. The material appeared pure by TLC (silica; 2% methanol/chloroform), $R_f=0.2$; (silica; 10% methanol/dichloromethane), $R_f=0.4$, IR (chloroform), $^1$H-NMR (CDCl$_3$) and MS (MH+ = 168) are consistent with the assigned structure.

ANALYSIS: Calculated for $C_9H_{13}NO_6$: 64.65%C; 7.83%H; 8.38%N; Found: 64.38%C; 7.81%H; 8.40%N.

EXAMPLE 2

1-Acetyl-4-ethynyl-4-(2-fluorophenylmethoxy)piperidine

Sodium hydride (39.98 g as a 50% mineral oil suspension, 883 mmole) was suspended in dry DMF (500 ml). 1-Acetyl-4-ethynyl-4-hydroxypiperidine (126.5 g; 758 mmole), dissolved in 500 ml of DMF, was added dropwise to the sodium hydride suspension at such a rate as to maintain the solvent temperature below 30° C. After evolution of hydrogen had ceased, 2-fluorobenzylchloride (120.8 g; 99 ml; 833 mmole), dissolved in 200 ml of DMF, was added dropwise, maintaining the temperature below 25° C. After allowing the mixture to react for 3 hours, 2 l. of water was added to quench the reaction. The mixture was extracted with ether and the combined ether extracts were back extracted with 5% hydrochloric acid. The organic phase was finally extracted with saturated aqueous sodium chloride and dried over anhydrous potassium carbonate. The mixture was filtered and the volatile components removed in vacuo. A residue of material, slightly impure by TLC, remained (193 g; 700 mmole; 84.3%). A 10 g sample was purified by preparative high performance liquid chromatography (HPLC) using hexane:ethylacetate (2:1) and finally ethylacetate as the effluents on silica gel. The residue was an oil which crystallized upon standing. Recovery was 7 g of material which appeared pure by TLC on silica gel in hexane:ethylacetate (2:1), $R_f=0.1$ and in chloroform:methanol (9:1), $R_f=0.6$, MS (ci MH+ =276), NMR-CDCl$_3$ and IR-CHCl$_3$ are consistent with the structure, m.p.=59°–62° C.

ANALYSIS: Calculated for $C_{16}H_{18}FNO_2$: 69.79%C; 6.60%H; 5.09%N; Found: 69.72%C; 6.56%H; 4.88%N.

EXAMPLE 3

4-(1-Oxoethyl)-4-(2-fluorophenylmethoxy)piperidine oxalate

The compound 1-acetyl-4-ethynyl-4-(2-fluorophenylmethoxy)piperidine (262 g; 950 mmole) was dissolved in 1600 ml of methanol:water (1:1) in a 3-necked round bottomed flask equipped with mechanical stirrer, thermometer, reflux condenser and nitrogen line. A solution of 180 ml of concentrated sulfuric acid dissolved in 200 ml of water was added to the stirred solution. The mixture was heated to reflux and stirred at that temperature for 3 hrs. Hydrolysis of the acetyl function was monitored by infra-red spectra of aliquots of the reaction. The reaction mixture was cooled and 73 g of mercuric sulfate was added and the temperature was raised to reflux again. Hydrolysis to the ketone was monitored by infrared spectra as well. After 3 hrs, at reflux, the reaction was determined to be complete. The mixture was cooled and filtered. The filtrate was made basic (pH=8.5) with 50% sodium hydroxide and was extracted several times with chloroform. The organic layer was dried over anhydrous magnesium sulfate and filtered. The solvent was removed under vacuum and the residue was chromatographed on 500 g of alumina packed in ether. The compound was eluted with ether:ethanol (1:1) with the collection of 125 ml fractions. Those containing the material (6–24) were combined and the oxalate salt was precipitated, which was filtered, washed with anhydrous ether and dried (42 g, 123 mmole, 13% yield). A 7 g sample was recrystallized from ethanol resulting in 2 g of 4-(1-oxoethyl)-4-(2-fluorophenylmethoxy)piperidine oxalate in the first crop. This material appeared pure by thin layer chromatography on silica gel in chloroform:methanol (9:1), $R_f=0.30$ and hexane:THF (1:1), $R_f=0.10$. MS (ci MH+ =252), NMR-DMSO-d$_6$ and IR-KBr are consistent with the structure, m.p.=154°–155° C.

ANALYSIS: Calculated for $C_{16}H_{20}FNO_6$: 56.79%C; 5.92%H; 4.10%N; Found: 56.60%C; 5.81%H; 4.01%N.

EXAMPLE 4

4-(1-Hydroxyethyl)-4-(2-fluorophenylmethoxy)piperidine oxalate

The compound 4-(1-oxoethyl)-4-(2-fluorophenylmethoxy)piperidine oxalate (10.00 g, 29.00 mmole) was converted to its free base with saturated aqueous sodium bicarbonate and extracted into chloroform. The organic layer was dried over anhydrous magnesium sulfate, filtered and the chloroform was removed in vacuo. The residue was dissolved in 20 ml of methanol and added dropwise to a suspension of 2.76 g of sodium-borohydride (73.00 mmole) in 30 ml of methanol. This was maintained at 20° C. (using an ice bath) and was allowed to react overnight at ambient temperature under nitrogen. The reaction was quenched with 5 ml of 10% hydrochloric acid. After being stirred for 1 hr., the solvent was removed under vacuum and the solid residue was dissolved in water. The solution was made basic (pH=10) with saturated, aqueous sodium bicarbonate and the mixture was extracted with chloroform. After drying over anhydrous magnesium sulfate, the chloroform solution was filtered, diluted with an equal volume of anhydrous ether and the product precipitated as its oxalate salt. The precipitate was recrystallized from 2-propanol resulting in 2.90 g of 4-(1-hydroxyethyl)-4-(2-fluorophenylmethoxy)piperidine oxalate (8.50 mmole, 28.15%) in the first crop. This material appeared pure by thin layer chromatography on silica gel in chloroform:methanol (1:1), $R_f=0.1$ and 2-propanol:ammonium hydroxide (7:3) $R_f=0.7$. MS (ci MH+ =254), NMR-DMSOd$_6$ and IR-KBr are consistent with the structure, m.p.=145°–150° C.

ANALYSIS: Calculated for $C_{16}H_{22}FNO_6$: 55.96%C; 6.47%H; 4.08%N; Found: 56.15%C; 6.38%H; 4.13%N.

EXAMPLE 5

2-Methyl spiro[2H-1,4-benzodioxepin-3(5H)4'-piperidine]hydrochloride

The compound 4-(1-hydroxyethyl)-4-(2-fluorophenylmethoxy)piperidine oxalate (55.4 g, 0.162 mole) was converted to its free base and was extracted into chloroform. The combined extracts were loaded onto a 500 g alumina column packed in diethyl ether. Final elution with diethyl ether:ethanol (1:1), removal of all solvents and trituration with hexane afforded 33 g (0.130 mole) solids after vacuum drying. Recovery=80.5%. The solids were dissolved in 290 ml dimethyl sulfoxide (DMSO). A second mixture was prepared by suspending a hexane-washed 50% mineral oil dispersion of NaH (6.6 g, 0.137 mole) in 340 ml dry DMSO. The second mixture was heated to 60°–70° C. for 1 hr. When evolution of hydrogen ceased, the mixture was cooled to 25° C. and the first solution added dropwise thereto while maintaining the temperature at about 25° C. When addition was complete, the mixture was heated to 70° C. for 1 hr. GLC showed the reaction to be substantially complete. The reaction mixture was quenched with $K_2CO_3/H_2O$ and extracted with diethyl ether. The extract was dried, and the hydrochloride salt was precipitated and dried at 50° C. in vacuo. Yield=32.2 g (0.12 mol), 91.9%.

EXAMPLE 6

7-Chloro-2-methylspiro[2H-1,4-benzodioxepin-3(5H)4'-piperidine]hydrochloride

The compound 2-methylspiro[2H-1,4-benzodioxepin-3(5H)4'-piperidine]hydrochloride (0.57 g, 2.12 mmole) was dissolved in 20 ml methanol and stirred with 0.32 g of N-chlorosuccinimide (2.33 mmole). The mixture was heated at reflux for 45 min. after which the reaction was determined to be 98% complete by GLC (3% ASI, 200° C., flow=45 ml/min). The volume of methanol was reduced by distillation and upon cooling the product crystallized. The reaction yielded 0.47 g of 7-chloro-2-methylspiro[2H-1,4-benzodioxepin-3(5H)4'-piperidine]-hydrochloride (1.55 mmole, 73.11%) which appeared pure by TLC on silica gel in 2-propanol:ammonium hydroxide (10:1), $R_f=0.4$ and in chloroform:methanol (1:1), $R_f=0.1$. MS (ci MH+ =268), NMR-DMSO-$d_6$, CMR-DMSO-$d_6$ and IR-KBr are consistent with the structure, m.p. 274°–276° C., d.

ANALYSIS: Calculated for $C_{14}H_{19}ClNO_6$: 55.27%C; 6.31%H; 4.60%N; Found: 54.;94%C; 6.24%H; 4.54%N.

EXAMPLE 7

7-Bromo-2-methylspiro[2H-1,4-benzodioxepin-3(5H)4'-piperidine]hydrochloride

The compound 2-methylspiro[2H-1,4-benzodioxepin-3(5H)4'-piperidine]hydrochloride (3.4 g, 12.64 mmole) was dissolved in 200 ml of methanol along with 2.47 g of NBS (13.9 mmole). The mixture was allowed to react for 45 min. after which time reaction was determined to be complete by GLC (OV 225, 200° C., 30 ml/min, $t_R=4.52$). The methanol was removed in vacuo and the residue was suspended in saturated aqueous $Na_2CO_3$. The products were extracted with chloroform and upon removal of solvent, in vacuo, there resulted a solid material. The solid was dissolved in ether and the hydrochloride salt precipitated. The material was recrystallized from methanol resulting in 2.5 g of 7-bromo-2-methylspiro[2H-1,4-benzodioxpin-3(5H)4'-piperidine]-hydrochloride which appeared, pure by TLC on silica gel in 2-propanol:ammonium hydroxide (9:1), $R_f=0.4$ and in chloroform:methanol (1:1), $R_f=0.1$. Mass Spec (M+ =311, 313; 1/1), NMR-DMSO-$d_6$ and IR-KBr are consistent with the structure, m.p.=290°–293° C., d.

ANALYSIS: Calculated for $C_{14}H_{19}BrClNO_2$: 48.22%C; 5.50%H; 4.02%N; Found: 48.13%C; 5.52%H; 3.99%N.

EXAMPLE 8

1'-[4,4-Bis-(4-fluorophenyl)butyl]-2-methylspiro[2H-1,4-benzodioxepin-3(5H)4'-piperidine]oxalate The compound 2-methylspiro[2H-1,4-benzodioxepin-3(5H)4'-piperidine]oxalate (3.9 g, 12.2 mmole) was converted to its free base and was extracted into chloroform. The combined extracts were dried over magnesium sulfate and were filtered. The filtrate was reduced in volume in vacuo. The residue was dissolved in 25 ml of DMF and was stirred with 2.6 g of 4,4-bis-(4-fluorophenyl)butylchloride (13.4 mmole). To the resultant mixture was added 2.5 g of milled anhydrous potassium carbonate and 16 mg of potassium iodide. The mixture was heated at 100° C. for 6 hr., after which time the reaction was determined complete by TLC. The mixture was cooled to ambient temperature and quenched with 100 ml water. The products were extracted with ether and the solvent was removed in vacuo. The residue was loaded onto an 80 g alumina column packed in ether. The products were eluted in 30 ml fractions. The desired compound was found in fraction numbers 2 and 3. The fractions were combined and the oxalate salt was precipitated, yielding 3.0 g (5.28 mmole 43.32%) of 1'-[4,4-bis-(4-fluorophenyl)butyl]-2-methylspiro[2H-1,4-benzodioxepin-3(5H)4'-piperidine]oxalate. The products were recrystallized from 2-propanol/methanol resulting in a crystalline material which appeared pure by TLC on silica gel in chloroform:methanol (9:1), $R_f=0.7$ and in dichloromethane:2-propanol, $R_f=0.4$. Mass Spec (ci MH+ =478), NMR-DMSO-$d_6$ and IR-KBr are consistent with the structure, m.p.=213°–214° C. (d).

ANALYSIS: Calculated for $C_{32}H_{35}F_2NO_6$: 67.70%C; 6.23%H; 2.47%N; Found: 67.51%C; 6.18%H; 2.29%N.

EXAMPLE 9

2-Methyl-1'-[3-[2-(4-fluorophenyl)-1,3-dioxolan-2-yl]propyl]spiro[2H-1,4-benzodioxepin-3(5H)4'-piperidine]maleate The compound 2-methylspiro[2H-1,4-benzodioxepin-3(5H)4'-piperidine]oxalate (5 g, 15.5 mmole) was converted to its free base and dried. The residue was dissolved in 50 ml of DMF and stirred with 4.2 g of γ-chloro-4-fluorobutyrophenone ethylene ketal (17.1 mmole), 5 g of potassium carbonate (anhydrous, milled) and 25 mg of potassium iodide. The mixture was heated to 100° C. under $N_2$ for 2 hrs. The reaction was determined complete by TLC. After cooling to ambient temperature, the mixture was quenched with water and was extracted with ether. The organic layers were combined and back extracted with saturated brine. The solvent was removed in vacuo and the residue loaded onto a 100 g alumina column packed in ether. Fractions of 50 ml of ether were eluted and the desired material was found in numbers 2–4. These fractions were combined and the maleate salt was precipitated. The solids were recrystallized from 2-propanol yielding 3.1 g of 2-methyl-1'-[3-[2-(4-fluorophenyl)-1,3-dioxalan-2-yl]propyl]spiro[2H-1,4-benzodioxepin-3(5H)4'-piperidine]maleate (5.6 mmole, 36%) which appeared pure by TLC on silica gel in chloroform:methanol (9:1), $R_f=0.4$ and in dichloromethane:2-propanol (1:1), $R_f=0.5$. MS (ci MH+ =442), NMR-DMSO-$d_6$ and IR-KBr are consistent with the structure, m.p.=154°–156° C.

ANALYSIS: Calculated for $C_{30}H_{36}FNO_8$: 64.61%C; 6.52%H; 2.51%N; Found: 64.39%C; 6.45%H; 2.57%N.

EXAMPLE 10

1'-[4,4-Bis(4-fluorophenyl)-3-butenyl]-2-methylspiro[2H-1,4-benzodioxepin-3(5H)4'-piperidine]maleate The compound 2-methylspiro[2H-1,4-benzodioxepin-3(5H)4'-piperidine]oxalate (5 g, 15.5 mmole) was converted to its free base and dried. The residue was dissolved in 50 ml of DMF and stirred with 4.8 g of 4,4-bis(4-fluorophenyl)-1-chloro-3-butene, 5 g of $K_2CO_3$ (anhydrous, milled) and 25 mg of potassium iodide under nitrogen. The mixture was quenched with water and extracted with ether. The ether extracts were combined and washed with saturated brine. The ether was removed in vacuo and the residue was loaded onto a 100 g alumina column packed in ether. Fractions of 50 ml of ether were eluted and the desired material found in maleate salt was precipitated. The material was washed with ether, filtered and vacuum dried, resulting in 2 g of 1'-[4,4-bis-(4-fluorophenyl)-3-butenyl]-2-methylspiro[2H-1,4-benzodioxepin-3-(5H)4'-piperidine]maleate (3.38 mole, 21.81%). This material appeared pure by TLC on silica gel in chloroform:methanol (9:1), $R_f=0.5$ and in dichloromethane:2-propanol (1:1), $R_f=0.8$. MS (ci MH+ =476), NMR-CDCl$_3$ and IR-CHCl$_3$ are consistent with the structure, m.p.=144°–149° C.(d).

ANALYSIS: Calculated for $C_{34}H_{35}F_2NO_6$: 69.01%C; 5.97%H; 2.37%N; Found: 68.67%C; 5.83%H; 2.44%N.

EXAMPLE 11

1'-(4,4-Diphenylbutyl)-2-methylspiro[2H-1,4-benzodioxepin-3(5H)4'-piperidine]oxalate The compound 2-methylspiro[2H-1,4-benzodioxepin-3(5H)4'-piperidine]hydrochloride (5 g, 18.55 mmole) was converted to its free base and dried. The oil was dissolved in 50 ml of DMF and stirred under nitrogen with 15 mg of potassium iodide, 5 g of potassium carbonate(milled, anhydrous) and 4.99 g of 4,4-diphenylbutylchloride (20.4 mmole) at ambient temperature, overnight. The reaction was determined to be complete by TLC. The mixture was quenched with water and extracted with ether. The solvent was removed in vacuo and the residue was loaded onto a 100 g alumina column packed in ether. Fractions of 50 ml were eluted and the desired material was found in numbers 2-5, which were combined. The oxalate salt was precipitated and recrystallized from 2-propanol/methanol. The resultant product, 2.4 g of 1'-[4,4-diphenylbutyl]-2-methylspiro[2H-1,4-benzodioxepin-3(5H)4'-piperidine]oxalate (4.52 mmole, 24.3%), appeared pure by TLC on silica gel in chloroform:methanol (9:1), $R_f$=0.5 and in dichloromethane-2-propanol (1:1), $R_f$0.4. MS (17 ev; M+ =441), NMR-DMSO-$d_6$ and IR-KBr are consistent with the structure, m.p. 192°–194° C.

ANALYSIS: Calculated for $C_{32}H_{37}NO_6$: 72.28%C; 7.03%H; 2.63%N; Found: 72.06%C; 7.03%H; 2.42%N.

EXAMPLE 12

1'-[4,4-Diphenyl-3-butenyl]-2-methylspiro[2H-1,4-benzodioxepin-3(5H)4'-piperidine]maleate The compound 2-methylspiro[2H-1,4-benzodioxepin-3(5H)4'-piperidine]hydrochloride (5 g, 18.6 mmole) was converted to its free base and dried. The resultant oil was dissolved in 50 ml of DMF and stirred with 5 g of potassium carbonate (milled, anhydrous), 15 mg of potassium iodide and 4.95 g of 4,4-diphenyl-3-butenyl chloride (20.4 mmole) for 2 days at ambient temperature under nitrogen. The reaction was determined to be complete by TLC and quenched with an equal volume of water. The products were extracted with ether and the combined extracts reduced in volume in vacuo. The remaining oil was loaded onto a 100 g alumina column packed in ether. Elution of 50 ml fractions resulted in the desired products being found in numbers 2-4. These fractions were combined and the maleate salt was precipitated. The solids were recrystallized from 2-propanol/methanol yielding 2.0 g of 1'-[4,4-diphenyl-3-butenyl]-2-methylspiro[2H-1,4-benzodioxepin-3(5H)4'-piperidine]maleate (3.6 mmole, 19.4%). This material appeared pure by TLC on silica gel in chloroform:methanol (9:1), $R_f$=0.6 and in dichloromethane:2-propanol (1:1), $R_f$=0.8. MS (ci MH+ =440), NMR-DMSO-$d_6$ and IR-KBr are consistent with the structure, m.p. 170°–171° C.

ANALYSIS: Calculated for $C_{34}H_{37}NO_6$: 73.48%C; 6.72%H; 2.52%N; Found: 73.38%C; 6.70%H; 2.56%N.

EXAMPLE 13

2-Methyl-1'-[3,3-diphenylpropyl]spiro[2H-1,4-dibenzodioxepin-3(5H)4'-piperidine]oxolate The compound 2-methylspiro[2H-1,4-benzodioxepin-3(5H)4'-piperidine]hydrochloride (5 g, 18.6 mmole) was dissolved in 100 ml of DMF and stirred along with 5 g of potassium carbonate (milled, anhydrous), 15 mg of potassium iodide and 4.7 g of 3,3-diphenylpropylchloride (20.41 mmole). The mixture was heated to 90° C. for 3 hrs. under nitrogen after which the reaction was determined to be complete by TLC. The reaction was quenched with water and extracted with ether. The extracts were combined, reduced in volume under vacuum and loaded onto a 100 g alumina column packed in ether. Fractions of 50 ml were collected and the desired product was found in numbers 2-5. These fractions were combined, after which the oxalate salt was precipitated. The solids were recrystallized from 2-propanol resulting in 2.6 g of 2-methyl-1'-[3,3-diphenylpropyl]-spiro-[2H-1,4-benzodioxepin-3(5H)4'-piperidine]oxalate (6.6 mmole, 35.42%) which appeared pure on TLC in chloroform:methanol (9:1), $R_f$0.6 and in dichloromethane:2-propanol (1:1), $R_f$=0.5, m.p.=178°–182° C. MS (ci MH+ =428), NMR-DMSO-$d_6$ and TR-KBr are consistent with the structure.

ANALYSIS: Calculated for $C_{31}H_{35}NO_6$: 71.92%C; 6.83%H; 2.70%N; Found: 72.09%C; 6.78%H; 3.16%N.

EXAMPLE 14

1'-[4-(4-Fluorophenyl)butyl]-2-methylspiro[2H-1,4-benzodioxepin-3(5H)4'-piperidine]hydrochloride The compound 2-methylspiro[2H-1,4-benzodioxepin-3(5H)4'-piperidine]hydrochloride (5 g, 18.6 mmole) was dissolved in 100 ml of DMF and stirred under nitrogen at 90° C. with 5 g of potassium carbonate (milled, anhydrous), 15 mg of potassium iodide, and 3.80 g of 4-(4-fluorophenyl)butyl chloride (20.4 mmole) overnight. The reaction was determined to be complete by TLC. The mixture was cooled to ambient temperature, quenched with water and extracted into ether. The ether extracts were backwashed with saturated brine and the solvent was removed under vacuum. The residue was loaded onto a 100 g alumina column packed in ether and 50 ml fractions were eluted. The desired material was found in fractions 2-4, which were subsequently combined. The hydrochloride was precipitated and recrystallized from methanol-water resulting in 2.4 g of 1'-[4-(4-fluorophenyl) butyl]-2-methylspiro[2H-1,4-benzodioxepin-3(5H)4'-piperidine]-hydrochloride (5.7 mmole, 30.78%) which appeared pure by TLC on silica gel in chloroform:methanol (9:1), $R_f$=0.8, and in dichloromethane:2-propanol (1:1), $R_f$=0.7. MS (MH+ =384), NMR-DMSO-$d_6$ and IR-KBr are consistent with the structure, m.p.=212°–213° C.

ANALYSIS: Calculated for $C_{24}H_{31}CLFNO_2$: 68.63%C; 7.45%H; 3.33%N; Found: 68.67%C; 7.49%H; 3.65%N.

EXAMPLE 15

1'-[4,4-Bis(4-chlorophenyl)butyl]-2-methylspiro[2H-1,4-benzodioxepin-3(5H)4'-piperidine]oxalate The compound 2-methylspiro[2H-1,4-benzodioxepin-3(5H)4'-piperidine]hydrochloride (4.0 g, 15.0 mmole) was dissolved in 150 ml of DMF. To the solution was added 4 g of potassium carbonate (milled, anhydrous), 15 mg of potassium iodide, and 5.12 g of 4,4-bis(4-chlorophenyl)butylchloride (15.0 mmole). The reaction mixture was stirred at 80° C., under nitrogen, overnight. The reaction was determined to be complete by TLC. The mixture was quenched with an equal volume of water and extracted with ether. The ether extracts were combined, backwashed with saturated brine and the solvent was removed under vacuum. The residue was loaded onto a 100 g alumina column packed into ether. Fractions of 50 ml were eluted and the desired product was found in numbers 3–5. These fractions were combined and the oxalate salt was precipitated. The solids were recrystallized from toluene-ethanol yielding 2.1 g of 1'-[4,4-bis(4-chlorophenyl)butyl]-2-methylspiro[2H-1,4-benzodioxepin-3(5H)4'-piperidine]oxalate (3.50 mmole, 23.3%). This material appeared pure by TLC on silica gel in chloroform:methanol (9:1), $R_f$=0.5 and in dichloro and IR-KBr are consistent with the structure, m.p. 192°–195° C.

ANALYSIS: Calculated for $C_{32}H_{35}Cl_2NO_6$: 63.99%C; 5.89%H; 2.33%N; Found: 63.68%C; 5.94%H; 2.25%N.

EXAMPLE 16

1'-[4,4-Diphenyl-3-butenyl]-7-chloro-2-methylspiro[2H-1,4-benzodioxepin-3(5H)4'-piperidine]oxalate The compound 7-chloro-2-methylspiro[2H-1,4-benzodioxepin-3(5H)4'-piperidine]hydrochloride (5 g, 16.5 mmole), 5 g of potassium carbonate (milled, anhydrous), 15 mg of potassium iodide and 4.39 g of 4,4-diphenyl-3-butenylchloride (18.1 mmole) were combined in 50 ml of DMF and stirred at 90° C. for 2 hr under nitrogen. The reaction was determined to be complete by TLC, after which time it was quenched with water and extracted with ether. The ether extracts were combined and the solvent was removed under vacuum. The residue was loaded onto a 100 g alumina column packed in ether. Fractions of 50 ml of ether were collected and the desired material was found in numbers 2–4. Combination of these fractions was followed by precipitation of the oxalate salt. The solids were recrystallized from 2-propanol/methanol resulting in 2 g of 1'-[4,4-diphenyl-3-butenyl]-7-chloro-2-methylspiro[2H-1,4-benzodioxepin-3(5H)4'-piperidine]oxalate (3.6 mmole, 21.6%) which appeared pure by TLC on silica gel in chloroform:methanol (9:1), $R_f$=0.5 and in dichloromethane:2-propanol (1:1), $R_f$=0.4. MS (ci MH+ =474), NMR-DMSO-d$_6$ and IR-KBr are consistent with the structure, m.p.=214°–215° C.

ANALYSIS: Calculated for $C_{32}H_{34}ClNO_6$: 68.13%C; 6.09%H; 2.48%N; Found: 67.95%C; 6.05%H; 2.45%N.

EXAMPLE 17

1'-[4,4-Diphenylbutyl]-7-chloro-2-methylspiro[2H-1,4-benzodioxepin-3(5H)4'-piperidine]oxalate The compound 7-chloro-2-methylspiro[2H-1,4-benzodioxepin-3(5H)4'-piperidine]hydrochloride (5 g, 16.5 mmole), 5 g of potassium carbonate (milled, anhydrous), 15 mg of potassium iodide and 4.43 g of 4,4-diphenylbutyl chloride (18.1 mmole) were combined in 50 ml of DMF. This mixture was stirred at 90° C. for 2 hr. under nitrogen. The reaction was determined to be complete by TLC, after which time it was quenched with water and extracted with ether. The ether extracts were combined and the solvent was removed under vacuum. The residue was loaded onto a 100 g alumina column packed in ether. Fractions of 50 ml were collected and the desired material was found in numbers 2–10. Combination of these fractions was followed by precipitation of the oxalate salt. The solids were recrystallized from 2-propanol-methanol resulting in 5.0 g of 1'-[4,4-diphenylbutyl]-7-chloro-2-methylspiro[2H-1,4-benzodioxepin-3(5H)4'-piperidine] oxalate (8.8 mmole, 53.52%) which appeared pure by TLC on silica gel in chloroform:methanol (9:1), $R_f$=0.5 and in dichloromethane:2-propanol (1:1), $R_f$=0.4. Mass Spec (MH+ =476), NMR-DMSO-d$_6$ and IR-KBr are consistent with the structure, m.p. =161°–165° C.

ANALYSIS: Calculated for $C_{32}H_{36}ClNO_6$: 67.89%C; 6.42%H; 2.47%N; Found: 67.64%C; 6.51%H; 2.36%N.

EXAMPLE 18

1'-[4,4-Bis(4-fluorophenyl)butyl]-7-chloro-2-methylspiro-[2H-1,4-benzodioxepin-3(5H)4'-piperidine]oxalate The compound 7-chloro-2-methylspiro[2H-1,4-benzodioxepin-3(5H)4'-piperidine]hydrochloride (5 g, 16.5 mmole) was dissolved in 100 ml of DMF and was stirred with 5 g of potassium carbonate (milled, anhydrous) for 1 hr. To the resultant mixture 15 mg of potassium iodide and 5.5 g of 4,4-bis(4-fluorophenyl)butyl chloride (19.6 mmole) was added. The mixture was stirred under a nitrogen atmosphere at 90° C. for 6 hr. The reaction was determined to be complete by GLC (OV 101:Temperature program:225° C. (2 min) rate=30°/min to 280° C. (20 min) flow ≈30 ml/min). The reaction mixture was cooled to ambient temperature, quenched with water and extracted with ether. The ether extracts were backwashed with saturated brine followed by removal of the solvent under vacuum. The residue was loaded onto a 100 g alumina column packed in ether. Fractions of 50 ml of ether were collected and the desired material was found to be in numbers 2–5. These fractions were combined and the oxalate salt of the product was precipitated. The white solids were recrystallized from 2-propanolmethanol resulting in 5.3 g of 1'-[4,4-bis(4-fluorophenyl)butyl]-7-chloro-2-methylspiro[2H-1,4benzodioxepin-3(5H)4'-piperidine]oxalate (8.8 mmole 53.50%) which appeared pure by TLC on silica gel in chloroform:methanol (9:1), $R_f$=0.5 and in dichloromethane:2-propanol (1:1), $R_f$=0.4. MS (MH+ =5.12), NMR-CDCl$_3$/DMSO-d$_6$ and IR-KBr are consistent with the structure, m.p.=170°–174° C.

ANALYSIS: Calculated for $C_{32}H_{34}ClF_2NO_6$: 63.83%C; 5.70%H; 2.33%N; Found: 63.66%C; 5.58%H; 2.21%N.

EXAMPLE 19

1'-[4,4-Bis(4-fluorophenyl)-3-butenyl]-7-chloro-2-methylspiro[2H-1,4-benzodioxepin-3(5H)4'-piperidine]-oxalate The compound 7-chloro-2-methylspiro[2H-1,4-benzodioxepin-3(5H)4'-piperidine]hydrochloride (5 g, 16.5 mmole) was dissolved in 100 ml of DMF and stirred with 5 g of potassium carbonate (milled,anhydrous) and 15 mg of potassium iodide. To the mixture was added 5 g of 4,4-bis(4-fluorophenyl)-3-butenyl chloride (18.1 mmole), and the mixture was stirred at ambient temperature overnight. TLC indicated that no reaction had occurred. The mixture was heated to 90° C. and after 3 hr products could be detected. Upon examination by GC/MS, it was determined that under these conditions the alkylating agent was not only reacting with the amine to form the desired product, but was also decomposing. The temperature of the reaction mixture was lowered to 55° C. The reaction was driven to completion through the addition of excess 4,4-bis(4-fluorophenyl)-3-butenyl chloride. Gas chromatographic conditions for the product were as follows: OV-101, 20 ml/min, temperature program, 225°–280° C., rate=30°

C./min, $t_R \approx 12.5$ min. The reaction was quenched with an equal volume of water and the products were extracted into ether. The extracts were combined, backwashed with saturated brine and reduced in volume under vacuum. The residue was loaded onto a 100 g alumina column packed in ether. Fractions of 50 ml were collected and the desired material was in fraction numbers 3-6. The appropriate fractions were combined and the oxalate salt precipitated. The solids were recrystallized from 2-propanol/methanol resulting in 2.3 g of 1'-[4,4-bis(4-fluorophenyl)-3-butenyl]-7-chloro-2-methylspiro[2H-1,4-benzodioxepin-3(5H)4'-piperidine]oxalate (3.8 mmole, 23.2%), which appeared pure by TLC on silica gel in chloroform:methanol (9:1), $R_f=0.6$ and in dichloromethane:2-propanol, (1:1), $R_f=0.5$. MS (MH+ =510), NMR-TFA and IR-KBr are consistent with the structure, m.p.=212°-214° C.

ANALYSIS: Calculated for $C_{32}H_{34}Cl_2NO_6$: 64.04%C; 5.39%H; 2.33%N; Found: 64.00%C; 5.45%H; 2.32%N.

EXAMPLE 20

7-Chloro-2-methyl-1'-(3,3-diphenylpropyl)spiro[2H-1,4-benzodioxepin-3(5H)4'-piperidine]hydrochloride The compound 7-chloro-2-methylspiro[2H-1,4-benzodioxepin-3(5H)4'-piperidine]hydrochloride (7.4 g, 24.3 mmole) was dissolved in 200 ml of DMF and stirred with 7.5 g of milled, anhydrous potassium carbonate. 3,3-Diphenylpropyl chloride (6.2 g, 26.7 mmole) and 25 mg of potassium iodide were added to the mixture, which was heated at 90° C. under nitrogen overnight. The reaction which was determined to be complete by TLC, was cooled and quenched with an equal volume of water. The products which were extracted into ether, were backwashed with saturated brine. The ether was removed under vacuum and the residue loaded onto a 200 g alumina column packed in ether. Fractions of 75 ml were collected and the desired material was found in numbers 4-7. These fractions were combined and the hydrochloride salt was precipitated. The material was recrystallized from toluene-ethylacetate resulting in 2 g of 7-chloro-2-methyl-1'-(3,3-diphenylpropyl)spiro[2H-1,4-benzodiozepin-3(5H)4'-piperidine]hydrochloride (4.0 mmole, 16.5%) which appeared pure by TLC on silica gel in chloroform:methanol (9:1), $R_f=0.6$ and in dichloromethane:2-propanol (1:1), $R_f=0.5$. A second crop (2.7 g, 5.2 mmole, 22.3%) was obtained having equal purity. MS (MH+ =261), NMR-CDCl₃ and IR-CHCl₃ are consistent with the structure, m.p.=224°-225° C., ANALYSIS: Calculated for $C_{29}H_{33}Cl_2NO_2$: 69.86%C; 6.69%H; 2.81%N; Found: 69.98%C; 6.60%H; 2.72%N.

EXAMPLE 21

7-Bromo-1'-[4,4-bis(4-fluorophenyl)butyl]-2-methyl-spiro-[2H-1,4-benzodioxepin-3(5H)4'-piperidine]oxalate The compound 7-bromo-2-methylspiro[2H-1,4-benzodioxepin-3(5H)4'-piperidine]hydrochloride (7.0 g, 20.1 mmole) was dissolved in 150 ml of DMF. The solution was stirred with 7.0 g of potassium carbonate (milled, anhydrous), 15 mg of potassium iodide and 6.2 g of 4,4-bis(4-fluorophenyl)butyl chloride (22.1 mmole) at 80° C. under nitrogen overnight. The reaction, which was determined to be complete by TLC, was cooled to ambient temperature, quenched with an equal volume of water, and extracted with ether. The ether extracts were combined and backwashed with saturated brine. The ether was removed under vacuum and the oily residue loaded onto a 140 g alumina colum packed in ether. Fractions of 50 ml were collected and the desired material was found in numbers 2-4. These fractions were combined and the oxalate salt precipitated. The solids, which were recrystallized from ethyl acetate/methanol, appeared to be pure 7-bromo-1'-[4,4-bis(4-fluorophenyl)-butyl]-2-methylspiro[2H-1,4-benzodioxepin-3(5H)4'-piperidine]oxalate (4.30 g, 6.7 mmole, 33.1%) by TLC on silica gel in chloroform:methanol (9:1), $R_f=0.5$ and in dichloromethane:2-propanol (1:1), $R_f=0.4$, MS (MH+ =556/558), NMR-DMSO-d₆ and IR-KBr are consistent with the structure, m.p.=183°-186° C.

ANALYSIS: Calculated for $C_{32}H_{34}BrF_2NO_6$: 59.44%C; 5.31%H; 2.17%N; Found: 59.25%H; 5.26%H; 2.19%N.

EXAMPLE 22

1'-[4-(4-Fluorophenyl)-4-oxobutyl]-2-methylspiro[2H-1,4-benzodioxepin-3(5H)4'-piperidine]oxalate The compound 2-methylspiro[2H-1,4-benzodioxepin-3(5H)4'-piperidine]hydrochloride (50 g, 185.5 mmole) was dissolved in 1.5 l of DMF and stirred under nitrogen with 50 g of milled, anhydrous potassium carbonate for 4 hr. To this mixture was added 50.3 g of γ-chloro-p-fluorobutyrophenone dimethyl ketal (204.1 mmole) and 0.15 g of potassium iodide. The resultant mixture was heated to 90° C. and allowed to react overnight, after which time the reaction was determined to be complete by TLC. The mixture was poured into water and the product extracted into ether. The ether extracts were combined, backwashed with saturated brine and reduced in volume under vacuum. The residue was dissolved in 800 ml of methanol and 300 ml of 3 N hydrochloric acid. The mixture was heated to reflux under nitrogen and stirred for 2 hr. The solution was cooled and reduced in volume under vacuum. The residue was suspended in saturated aqueous sodium carbonate and extracted into ether. The extracts were combined, backwashed with saturated brine and dried over anhydrous potassium carbonate. The ether was removed under vacuum from the extract and the residue loaded onto a 1000 g alumina column packed in ether. Fractions of 500 ml of ether were collected and the desired product was found in numbers 2-4, which were combined. The oxalate salt was precipitated and recrystallized from 2-propanol, resulting in 28.6 g of 1'-[4-(4-fluorophenyl)-4-oxobutyl]-2-methylspiro[2H-1,4-benzodioxepin-3(5H)4'-piperidine]oxalate (58.7 mmole, 31.6%) which appeared pure by TLC on silica gel in chloroform:methanol (9:1), $R_f=0.5$ and dichloromethane:2-propanol (1:1), $R_f=0.4$, m.p.=134°-137° C. MS (MH+ =488), NMR-DMSO-d₆ and IR-KBr are consistent with the structure.

ANALYSIS: Calculated for $C_{26}H_{30}FNO_7$: 64.05%C; 6.21%H; 2.87%N; Found: 63.72%C; 6.15%H; 2.90%N.

EXAMPLE 23

1'-[4-Hydroxy-4-(4-fluorophenyl)butyl]-2-methylspiro-[2H-1,4-benzodioxepin-3(5H)4'-piperidine]

The compound 1'-[4-(4-fluorophenyl)-4-oxobutyl]-2-methylspiro[2H-1,4-benzodioxepin-3(5H)4'-piperidine]oxalate (15 g, 30.8 mmole) was converted to its free base and dried. The residue was dissolved in 50 ml of ethanol and stirred with 0.8 g of sodium borohydride (pellets) under a nitrogen atmosphere, over the weekend, at ambient temperature. The mixture was stirred with 40 ml of 3 N HCl which resulted in the formation of solids. The solids were insoluble in water and could be recrystallized from ethyl acetate (8.7 g, 20.0 mmole, 65.0%). Upon treatment with saturated sodium carbonate solution and chloroform, all solids were dissolved. After drying the organic phase, and the removal of the solvent, there remained a crystalline solid which could be recrystallized from chloroform/hexane. The material was identified as 1'-[4-hydroxy-4-(4-fluorophenyl)butyl]-2-methylspiro[2H-1,4-benzodioxepin-3(5H)4'-piperidine]. The compound appeared pure by TLC on silica gel in chloroform:methanol (9:1), $R_f=0.5$, and in dichloromethane:2-propanol, (1:1), $R_f=0.4$. MS (MH+=400), NMR-CDCl$_3$ and IR-CHCl$_3$ are consistent with the structure, m.p. =143°-146° C.

ANALYSIS: Calculated for $C_{24}H_{30}FNO_3$: 72.14%C; 7.58%H; 3.50%N; Found: 72.00%C; 4.49%H; 3.38%N.

EXAMPLE 24

1'-[4-(4-Fluorophenoxy)-4-(4-fluorophenyl)butyl]-2-methylspiro[2H-1,4-benzodioxepin-3(5H)4'-piperidine]oxalate Sodium hydride (0.96 g of a 50% mineral oil suspension, 0.02 mole) was hexane washed, suspended in 80 ml of DMSO and heated to 60°-70° C. until evolution of hydrogen ceased. The mixture was cooled to 5° C. and to it was added a solution of 6.8 g of 1'-[4-hydroxy-4-(4-fluorophenyl)butyl]-2-methyl-spiro[2H-1,4-benzodioxepin-3(5H)4'-piperidine] dissolved in 225 ml of DMSO. The mixture was stirred at ambient temperature for 15 min. after which 8.0 g of 1,4-difluorobenzene (0.07 mole) was added. The mixture was heated to 70° C. and maintained at that temperature overnight. TLC indicated 50-60% completion of reaction which was not improved by heating at 80° C. The mixture was cooled to ambient temperature and quenched with an equal volume of water. The products were extracted into ether and backwashed with saturated brine. The ether was removed under vacuum and the residue purified by preparative HPLC using two silica gel columns (2×500 cc), eluting with hexane:ether:methanol (10:10:1). The desired material was detected by refractive index and ultraviolet absorption. The fractions which contained the product were combined and the solvent removed under vacuum. The oil residue was dissolved in ether and the oxalate salt precipitated. The solids were recrystallized from ethylacetate:methanol. The resultant 1'-[4-(4-fluorophenoxy)-4-(4-fluorophenyl)butyl]-2-methylspiro-[2H-1,4-benzodioxepin-3(5H)4'-piperidine]oxalate (3.9 g, 7.9 mmole 39.5%) appeared pure by TLC on silica gel in chloroform:methanol (9:1), $R_f=0.5$ and in hexane:ether:methanol (10:10:1), $R_f=0.3$. MS (MH+=494), NMR-DMSO-d$_6$, CMR-DMSO-d$_6$ and IR-KBr are consistent with the structure, m.p.=180°-182° C.

ANALYSIS: Calculated for $C_{32}H_{35}F_2NO_3$: 65.85%C; 6.06%H; 2.40%N; Found: 66.05%C; 6.07%H; 2.27%N.

EXAMPLE 25

1-Acetyl-4-ethynyl-4-(2,5-difluorophenylmethoxy)piperidine

A solution of 7.0 g of potassium t-butoxide (62.5 mmole) in 20 ml of dry DMF was added dropwise to a chilled solution of 10 g of 1-acetyl-4-ethynyl-4-hydroxypiperidine (59.9 mmole) in 75 ml of dry DMF, at such a rate as to maintain the temperature at 10° C. The mixture was allowed to equilibrate at 10° C. for 15 min. after which time it was cooled to −20° C. After complete addition the reaction mixture was warmed to 0° C. and allowed to react for 1 hr. The reaction appeared to be complete by GLC and was quenched with ice and water. The products were extracted into ether and dried over K$_2$CO$_3$. After filtration the solvent was removed under vacuum. The crystalline product was recrystallized from cyclohexane and dried, affording 10.5 g of 1-acetyl-4-ethynyl-4-(2,5-difluorophenylmethoxy)piperidine (35.8 mmole, 59.83%). This material appeared pure by GLC (99% on OV225, temperature program: 200° C. (2 min.), rate=25° C./min., 250° C. (15 min.), flow=30 ml/min. $t_R$=4.00 min.) and by TLC on silica gel in hexane:ethylacetate (1:1), $R_f=0.2$. Mass Spec (ci MH+=294), NMR-CDCl$_3$ and IR-CHCl$_3$ are consistent with the structure, m.p.=90°-93° C.

ANALYSIS: Calculated for $C_{16}H_{17}F_2NO_2$: 65.51%C; 5.85%H; 4.77%N; Found: 65.72%C; 5.87%H; 4.68%N.

EXAMPLE 26

4-(1-Oxoethyl)-4-(2,5-difluorophenylmethoxy)piperidine hydrochloride

The compound 1-acetyl-4-ethynyl-4-(2,5-difluorophenylmethoxy)piperidine (5 g, 17.1 mmole) was suspended in 50 ml of 15% sulfuric acid. The mixture was heated at reflux under nitrogen for 1 hr. after which complete dissolution occurred. Mercuric sulfate (0.25 g, freshly opened) was added to the cooled solution. The mixture was heated at 65° C. overnight. The reaction was determined to be 98% complete by GLC. The mixture was basified with saturated aqueous sodium carbonate and extracted with chloroform. The organic extracts were combined, dried over K$_2$CO$_3$ and filtered through celite. The filtrate was reduced in volume under vaccum and the residue dissolved in ether. The hydrochloride salt was precipitated and recrystallized from ethylacetate/ethanol, yielding, in two crops, 3.2 g of 4-(1-oxoethyl)-4-(2,5-difluorophenylmethoxy)piperidine hydrochloride (10.48 mmole, 61.4%) which appeared pure by GLC (OV225, temperature program 200° C. (2 min.), rate=25°/min., 250° C. (15 min.), flow=30 ml/min., $t_R$=1.59) and by TLC on silica gel in 2-propanol:ammonium hydroxide (8:2), $R_f=0.8$. MS (ci MH+=270), NMR-DMSO-d$_6$ and IR-KBr are consistent with the structure, m.p.=197°-201° C.

ANALYSIS: Calculated for $C_{14}H_{18}ClF_2NO_2$: 54.99%C; 5.95%H; 4.58%N; Found: 55.03%; 5.88%H; 4.70%N.

EXAMPLE 27

4-(1-Hydroxyethyl)-4-(2,5-difluorophenylmethoxy)piperidine

The compound 4-(1-oxoethyl)-4-(2,5-difluorophenylmethoxy)piperidine hydrochloride (5 g, 16.4 mmole) was dissolved in 50 ml of water. The pH was adjusted to 8.5 using 50% sodium hydroxide. Sodium borohydride (0.2 g, 4.5 mmole) was added to the solution and the mixture was allowed to react for ½ hr. The reaction was determined to be complete by GLC. The reaction mixture was saturated with potassium carbonate and extracted with ether. The ether extracts were combined, dried, and filtered. The solvent was removed under vacuum resulting in 4 g of solid white material. This solid was recrystallized from cyclohexane resulting in 3.5 g of 4-(1-hydroxyethyl)-4-(2,5-difluorophenylmethoxy)piperidine (12.9 mmole, 78.7%) which appeared pure by GLC (OV225, temperature program: 200° C. (2 min.), rate=25° /min., 250° C. (15 min.), flow=30 ml/min., $t_R$=2.31) and by TLC on silica gel in 2-propanol:ammonium hydroxide (8:2), $R_f$=0.5. MS (ci MH+=272). NMR-CDCl3 and IR-CHCl3 are consistent with the structure. m.p.=94°–96° C.

ANALYSIS: Calculated for $C_{14}H_{19}F_2NO_2$: 61.97%C; 7.07%H; 5.16%N; Found: 61.92%C; 7.26%H; 5.00%N.

EXAMPLE 28

7-Fluoro-2-methyl spiro[2H-1,4-benzodioxepin-3(5H)4'-piperidine]hydrochloride

The compound 4-(1-hydroxyethyl)-4-(2,5-difluorophenylmethoxy)piperidine (84.4 g, 311.0 mmole) was dissolved in 510 ml of dry THF and stirred with 36.6 g of potassium tert-butoxide (326.0 mmole). The mixture was heated at reflux under nitrogen for 8 hrs, after which a 10% excess of potassium tert-butoxide was added. The mixture was treated 6 hrs, after which the reaction was determined to be complete by GLC. The mixture was cooled and quenched with saturated aqueous sodium carbonate. The product was extracted into ether and dried over potassium carbonate. The dried ether extracts were filtered and the hydrochloride salt was precipitated. The solids were filtered, dried (85.0 g, 287.0 mmole, 92.9%), and recrystallized from ethylacetate/ethanol. The resultant crystals were filtered and vacuum dried at 60° C. resulting in 62.6 g of 7-fluoro-2-methylspiro [2H-1,4-benzodioxepin-3(5H)4'-piperidine]hydrochloride (218.0 mmole, 70.01%). The material appeared pure by GLC (OV225, flow=30 ml/min., temperature program: 200° C. (2 min.), rate=25° C./min., silica gel in 2-propanol:ammonium-hydride (8:2), $R_f$=0.5. MS (ci MH+=251), NMR-DMSO-d6 and IR-KBr are consistent with the structure, m.p.=273°–277° Cd.

ANALYSIS: Calculated for $C_{14}H_{19}ClFNO_2$: 58.43%C; 6.67%H; 4.86%N; Found: 58.30%C; 6.54%H; 4.80%N.

EXAMPLE 29

1'-(4,4-Diphenylbutyl)-7-fluoro-2-methyl spiro-[2H-1,4-benzodioxepin-3(5H)4'-piperidine]hydrochloride 7-Fluoro-2-metyl spiro[2H-1,4-benzodioxepin-3(5H)4'-piperidine]hydrochloride (5 g, 17.4 mmole) was dissolved in 100 ml of DMF and stirred with 5 g of milled, anhydrous potassium carbonate, 15 mg of potassium iodide and 4.7 g of 4,4-diphenylbutylchloride (19.1 mmole) at 65° C. under nitrogen overnight. The reaction which was determined to be complete by TLC was cooled, quenched with an equal volume of water and extracted with ether. The ether extracts were combined and backwashed with saturated sodium chloride. The solvent was removed under vacuum. The oily residue was loaded onto a 100 g alumina column packed with ether. Fractions of 50 ml were collected and the desired material was found in numbers 2–3. These fractions were combined and the solvent was removed under vacuum. The residual oil was dissolved in anhydrous ether and the hydrochloride salt precipitated. Recrystallization from toluene/ethyl acetate/ethanol afforded 3.0 g (6.1 mmole, 34.8%) of 1'-(4,4-diphenylbutyl)-7-fluoro-2-methyl spiro[2H-1,4-benzodioxepin-3(5H)4'-piperidine]-hydrochloride which appeared pure by TLC on silica gel in dichloromethane:methanol (9:1), $R_f$=0.6 and in dichloromethane:2-propanol (1:1), $R_f$=0.5. MS (ci MH+=460). NMR-DMSO-d6 and IR-KBr are consistent with the structure. m.p.=215°–218° C.

ANALYSIS: Calculated for $C_{30}H_{35}ClFNO_2$: 72.63%C; 7.13%H; 2.82%N; Found: 72.73%C; 6.74%H; 2.56%N.

EXAMPLE 30

1'-[4,4-Bis-(4-fluorophenyl)butyl]-7-fluoro-2-methyl-spiro[2H-1,4-benzodioxepin-3(5H)4'-piperidine]hydrochloride 7-Fluoro-2-methylspiro[2H-1,4-benzodioxepin-3(5H)4'-piperidine]hydrochloride (5.0 g, 17.4 mmole) was dissolved in 100 ml of DMF and stirred with 5 g of milled, anhydrous potassium carbonate, 15 mg potassium iodide and 5.4 g of 4,4-bis(4-fluorophenyl)butylchloride (19.1 mmole) at 65° C. under nitrogen overnight. The reaction which was determined to be complete by TLC, was cooled, quenched with an equal volume of water and extracted with ether. The ether extracts were combined and back-washed with saturated brine. The solvent was removed under vacuum. The oily residue was loaded onto a 100 g alumina column packed in ether. Fractions of 50 ml were collected and the desired product was found in numbers 2–4. These fractions were combined and the solvent was removed under vacuum. The residual oil was dissolved in anhydrous ether and the hydrochloride salt precipitated. Recrystallization from toluene ethyl acetate/ethanol afforded 5.9 g (7.3 mmole, 42.2%) of 1'-[4,4-bis(4-flluorophenyl)butyl]-7-fluoro-2-methylspiro-[2H-1,4-benzodioxepin-3(5H)4'-piperidine]hydrochloride which appeared pure by TLC on silica gel in dichloromethane:methanol (9:1), $R_f$=0.6 and in dichloromethane:2-propanol (1:1), $R_f$=0.5. MS (ci MH+=496), NMR-DMSO-d6 and IR-KBr are consistent with the structure, m.p.=162°–165° C.

ANALYSIS: Calculated for $C_{30}H_{33}ClF_3NO_2$: 67.72%C; 6.26%H; 2.63%N; Found: 67.35%C; 5.95%H; 2.56%N.

In Examples 31 to 36, an alternate method for preparing the compound of formula (+7) in FIG. 1 is described. The 1-methyl-4-ethynyl-4-hydroxypiperidine employed as starting material in Example 31 can be prepared by the method disclosed in N. Barbulescu, C. Bornaz and C. Greff, Rev. Chim. (Bucharest) 20 (6): 373–374 (1969).

EXAMPLE 31

1-Methyl-4-ethynyl-4-(2-fluorophenylmethoxy)piperidine oxalate

To a stirred suspension of 7.8 g of NaH (163.0 mmole, 50% in oil; washed three times with hexane) in 80 ml dry DMF was added dropwise a solution of 20 g (144.0 mmole) of 1-methyl-4-ethynyl-4-hydroxy piperidine in 120 ml of DMF. The solution was allowed to cool to room temperature and, subsequently, 20 ml (169.0 mmole) of 2-fluorobenzyl chloride was added dropwise. The mixture was allowed to stir overnight, poured slowly into water, extracted twice with ether, washed with saturated sodium chloride, dried over potassium carbonate, filtered and the solvent evaporated, yielding 1-methyl-4-ethynyl-4-(2-fluorophenylmethoxy)piperidine oxalate (35.2 g 104.0 mmole, 72.0%).

ANALYSIS: Calculated for $C_{15}H_{18}FNO \cdot C_2H_2O_4$: 60.70%C; 6.01%H; 4.16%N; Found: 60.42%C; 5.97%H; 4.08%N.

EXAMPLE 32

4-(1-Oxoethyl)-4-(2-fluorophenylmethoxy)-1-methylpiperidine oxalate

To a suspension of 1-methyl-4-(2-fluorophenylmethoxy)-piperidine (liberated from 30.6 g, 90.7 mmole, of the oxalate, and 165 ml of water was added a solution of 22 ml of conc. sulfuric acid in 53 ml of water. To the solution was added 4.0 g (13.4 mmole) of mercuric sulfate. The mixture was heated at reflux for 1.5 hr. under nitrogen and allowed to cool to room temperature. The mixture was poured into cold saturated sodium carbonate, extracted twice with ether and washed with saturated sodium chloride. The ether solution was dried over anhydrous potassium carbonate, filtered and the solvent evaporated to provide an oil. The oxalate salt was precipitated, and recrystallization from methanol/ethanol provided 21.1 g (59.4%) of 4-(1-oxoethyl)-4-(2-fluorophenylmethoxy)-1-methyl piperidine oxalate. The material appeared pure by TLC on silica gel in methanol:methylene chloride (9:1), $R_f=0.4$ and on alumina in ether, $R_f=0.3$. IR (Nujol), NMR-DMSO-$d_6$ and MS (ci MH+ =266) are consistent with the structure, m.p. = 180°–181° C.

ANALYSIS: Calculated for $C_{15}H_{20}FNO_2 \cdot C_2H_2O_4$: 57.45%C; 6.24%H; 3.94%N; Found: 57.25%C; 6.26%H; 3.82%N.

EXAMPLE 33

4-(1-Hydroxyethyl)-4-(2-fluorophenylmethoxy)-1-methylpiperidine oxalate

Sodium borohydride (533 g, 1.4 mole) was dissolved in 4500 ml methanol. To the resulting solution was added, with stirring, a solution of 4-(1-oxoethyl)-4-(2-fluorophenylmethoxy)-1-methylpiperidine (151 g, 0.6 mole) in 500 ml methanol. The reaction was allowed to proceed at 0° C. for 1.5 hrs. The reaction mixture was made basic with 3 l. of saturated aqueous $Na_2CO_3$ causing a precipitate to form. To the mixture was added 2 l. diethyl ether. The resulting solution was worked up with cold water and diethyl ether and the diethyl ether extracts were combined. The oxalate salt was precipitated and recrystallized from 2-propanol. After recrystallization, filtration and drying in vacuo at 45° C., 32 g of 4-(1-hydroxyethyl)4-(2-fluorophenylmethoxy)-1-methylpiperidine oxalate were obtained. MS (ci MH+ =268), NMR-DMSO$d_6$ and IR-KBr were consistent with the structure, m.p. = 104°–106° C.

ANALYSIS: Calculated for $C_{14}H_{24}NO_6F$: 57.12%C; 6.78%H; 3.92% N; Found: 56.65%C; 6.72%H; 3.77%N.

EXAMPLE 34

1', 2-dimethylspiro[2H-1,4-benzodioxepin-3(5H)4-piperidine]oxalate

The free base of 4-(1-hydroxyethyl)-4-(2-fluorophenylmethoxy)-1-methylpiperidine was generated from its oxalate with saturated sodium bicarbonate and extracted into chloroform. This was dried over anhydrous sodium sulfate, taken to dryness, weighed (30.3 g, 115.0 mmole) and dissolved in 300 ml of dry dimethylformamide. This solution was added dropwise and under nitrogen to a stirred suspension of hexane washed sodium hydride (6.5 g 50% mineral oil suspension, 136.0 mmole). The mixture was heated to 130° C. and stirred for 0.5 hr. The reaction was quenched, when conversion was greater than 90% by GLC (3% ASI column, flow=45 ml/min, 200° C.), by adding ice and water. The products were isolated by ether extraction. The extracts were dried over anhydrous potassium carbonate, filtered and the oxalate salt precipitated. Recrystallization was carried out in methanol resulting in 11.1 g of 1',2-dimethylspiro[2H-1,4-benzodioxepin-3(5H)4'-piperidine]oxalate. The material appeared pure by thin layer chromatography on silca gel in chloroform:methanol (1:1), $R_f=0.25$ and on alumina in chloroform:methanol (95:5), $R_f=0.90$. MS (ci MH+ =248), IR-KBr and NMR-DMSO-$d_6$ are consistent with the structure. m.p. = 162°–165° C.

ANALYSIS: Calculated for $C_{15}H_{21}N_1O_2 \cdot C_2H_2O_4$: 60.53%C; 6.82%H; 4.15%N; Found: 60.26%C; 6.85%H; 4.10%N.

EXAMPLE 35

1'-(Phenoxycarbonyl)-2-methylspiro[B 2H-1,4-benzodioxepin-3(5H)4'-piperidine]

The compound 1',2-dimethylspiro[2H-1,4-benzodioxepin-3(5H)4'-piperidine] (194.4 g, 787.0 mmole) was dissolved with stirring under a nitrogen blanket in 2 l. of dichloromethane. Anhydrous $K_2CO_3$ (131 g) was added to the resulting solution. Phenoxycarbonyl chloride (147.1 g, 930.0 mmole) was then added with stirring. The resulting mixture was allowed to react overnight at ambient temperature. After successive acidic and alkaline washes, the mixture was dried over $MgSO_4$, filtered and taken to dryness. A 10 g sample of the product was loaded onto a column of silica gel (100 g) packed in chloroform, and thirteen 75 ml fractions were recovered. Mass spectra showed the compound to be in fractions 5–11. These fractions were combined and taken to dryness. The oily residue was crystallized from hexane-cyclohexane resulting in 1.55 g of 1'-phenoxycarbonyl-2-methylspiro[2H-1,4-benzodioxepin-3(5H)4'-piperidine] which appeared pure by TLC in chloroform:methanol (95:5), $R_f=0.4$, MS (ci MH+ =354), NMR-$CDCl_3$ and IR-$CHCl_3$ are consistent with the structure, m.p. = 85°–89° C.

ANALYSIS: Calculated for $C_{21}H_{23}NO_4$ 71.36%C; 6.57%H; 3.96%N; Found: 71.31%C; 6.60%H; 3.96%N.

EXAMPLE 36

2-Methylspiro[2H-1,4-benzodioxepin-3(5H)4'-piperidine]-oxalate

1'-Phenoxycarbonyl-2-methylspiro[2H-1,4-benzodioxepin-3(5H)4'-piperidine] (44.0 g, 130.0 mmole) was dissolved in 230 ml methanol, to which was added 128.2 ml of 15% aqueous sodium hydroxide. With stirring under nitrogen, the mixture was heated to 60° C. and maintained at that temperature for 18 hrs. The mixture was cooled to room temperature and extracted with chloroform. The chloroform extracts were combined and dried over anhydrous potassium carbonate, filtered and taken to dryness. The residue was dissolved in ethanol:ether (1:1) and the oxalate salt precipitated (11.9 g, 0.037 mole, 28.31%). A 5 g sample was recrystallized from ethanol yielding 2.5 g of material which appeared pure by thin layer chromatography on silica gel in chloroform:methanol (1:1), $R_f$=0.1 and ethanol:ammonium hydroxide (7:3), $R_f$=0.85. MS (ci MH+ =234), IR-KBr and NMR-DMSO-$d_6$ were all consistent with the structure, m.p.=216°–218° C.

ANALYSIS: Calculated for $C_{15}H_{21}N_1O_2 \cdot C_2H_2O_4$: 60.53%C; 6.82%H; 4.15%N; Found: 60.26%C; 6.85%H; 4.10%N.

EXAMPLE 37

1-Acetyl-4-ethynyl-4-(2,5-difluorophenylmethoxy)-piperidine

A solution of 7.04 g of potassium t-butoxide (62.9 mmole) in 20 ml of dry DMF was added dropwise to a chilled solution of 10 g of 1-acetyl-4-ethynyl-4-hydroxypiperidine (59.9 mmole) in 75 ml of dry DMF, at such a rate as to maintain the temperature at 10° C. The mixture was allowed to equilibrate at 10° C. for 15 min. after which time it was cooled to −20° C. To this solution was added 9.73 g of 2,5-difluorobenzylchloride (59.9 mmole) at such a rate as to maintain the temperature around −20° C. After complete addition, the reaction mixture was warmed to 0° C. and allowed to react for 1 hr. The reaction appeared to be complete by GLC and was quenched with ice and water. The products were extracted into ether and dried over $K_2CO_3$. After filtration, the solvent was removed under vacuum. The crystalline product was recrystallized from cyclohexane and dried, affording 10.5 g of 1-acetyl-4-ethynyl-4-(2,5-difluorophenylmethoxy)piperidine (35.8 mmole, 59.83%). This material appeared pure by GLC (99% on OV225, temperature program: 200° C. (2 min), rate=25° C./min, 250° C. (15 min), flow=30 ml/min $t_R$=4.00 min) and by TLC on silica gel in hexane:ethylacetate (1:1), $R_f$=0.2. MS (ci MH+ =294), NMR-$CDCl_3$ and IR=$CHCl_3$ were consistent with the structure; m.p.=90°–93° C.

ANALYSIS: Calculated for $C_{16}H_{17}F_2NO_2$: 65.51%C; 5.85%H; 4.77%N; Found: 65.72%C; 5.87%H; 4.68%N.

EXAMPLE 38

4-(1-Oxoethyl)-4-(2,5-difluorophenylmethoxy)piperidine hydrochloride

The compound 1-acetyl-4-ethynyl-4-(2,5-difluorophenylmethoxy)piperidine (5 g, 17.06 mmole) was suspended in 50 ml of 15% sulfuric acid. The mixture was heated at reflux under nitrogen for 1 hr, after which complete dissolution occurred. Mercuric sulfate (0.25 g, freshly opened) was added to the cooled solution. The mixture was heated at 65° C. overnight. The reaction was determined to be 98% complete by GLC. The mixture was basified with saturated aqueous sodium carbonate and extracted with chloroform. The organic extracts were combined, dried over $K_2CO_3$ and filtered through celite. The filtrate was reduced in volume under vacuum and the residue dissolved in ether. The hydrochloride salt was precipitated and recrystallized from ethylacetate/ethanol, yielding, in two crops, 3.2 g of 4-(1-oxoethyl)-4-(2,5-difluorophenylmethoxy)piperidine hydrochloride (10.48 mmole, 61.4%), which appeared pure by GLC (OV225, temperature program 200° C. (2 min), rate=25° /min, 250° C. (15 min), flow=30 ml/min, $t_R$=1.59) and by TLC on silica gel in 2-propanol:ammonium hydroxide (8:2), $R_f$=0.8. MS (ci MH+ =270), NMR-DMSO-$d_6$ and IR-KBr were consistent with the structure; m.p.=197°–201° C.

ANALYSIS: Calculated for $C_{14}H_{18}ClF_2NO_2$: 54.99%C; 5.95%H; 4.58%N; Found: 55.03%C; 5.88%H; 4.70%N.

EXAMPLE 39

4-(1-Hydroxyethyl)-4-(2,5-difluorophenylmethoxy)-piperidine

The compound 4-(1-oxoethyl)-4-(2,5-difluorophenylmethoxy) piperidine hydrochloride (5 g, 16.4 mmole) was dissolved in 50 ml of water. The pH was adjusted to 8.5 using 50% sodium hydroxide. Sodium borohydride (0.2 g, 4.5 mmole) was added to the solution and the mixture was allowed to react for ½ hour. The reaction was determined to be complete by GLC. The reaction mixture was saturated with potassium carbonate and extracted with ether. The ether extracts were combined, dried and filtered. The solvent was removed under vacuum resulting in 4 g of solid white material. This solid was recrystallized from cyclohexane resulting in 3.5 g of 4-(1-hydroxyethyl)-4-(2,5-difluorophenylmethoxy)piperidine (12.9 mmole, 78.7%), which appeared pure by GLC (OV225, temperature program: 200° C. (2 min) rate=25° /min 250° C. (15 min) flow=30 ml/min $t_R$=2.31) and by TLC on silica gel in 2-propanol:ammonium hydroxide (8:2) $R_f$=0.5, MS (ci MH+ =272), NMR-$CDCl_3$ and IR-$CHCl_3$ were consistent with the structure: m.p.=94°–96° C.

ANALYSIS: Calculated for $C_{14}H_{19}F_2NO_2$: 61.97%C; 7.07%H; 5.16%N; Found: 61.92%C; 7.26%H; 5.00%N.

EXAMPLE 40

7-Fluoro-2-methylspiro[2H-1,4-benzodioxepin-3(5H)4'-piperidine]hydrochloride

The compound 4-(1-hydroxyethyl)-4-(2,5-difluorophenylmethoxy)piperidine (84.4 g, 0.311 mole) was dissolved in 510 ml of dry THF and stirred with 36.6 g of potassium tert-butoxide (0.326 mole). The mixture was heated at reflux under nitrogen for 8 hr after which a 10% excess of potassium tert-butoxide was added. The mixture was heated 6 hr after which the reaction was determined to be complete by GLC. The mixture was cooled and quenched with saturated aqueous sodium carbonate. The product was extracted into ether and dried over potassium carbonate. The dried ether extracts were filtered and the hydrochloride salt was precipitated. The solids were filtered, dried (83.0 g, 0.289 mole, 92.83%) and recrystallized from ethyl acetate/ethanol. The resultant crystals were filtered and vacuum dried at 60° C. resulting in 62.6 g of 7-fluoro-2-methylspiro[2H-1,4-benzodioxepin-3(5H)4'-piperidine]hydrochloride (0.218 mole 70.01%). This material appeared pure by GLC (OV225, flow=30 ml/min, temperature program: 200° C. (2 min), rate=25° C. (15 min), $t_R$=1.82) and TLC on silica gel in 2-propanol:ammonium hydroxide (8:2), $R_f$=0.5. MS (ci MH+ =251), NMR-DMSO-$d_6$, and IR-KBr were consistent with the structure; m.p.=273°–277° C.(d).

ANALYSIS: Calculated for $C_{14}H_{19}ClFNO_2$: 58.43%C; 6.67%H; 4.86%N; Found: 58.30%C; 6.54%H; 4.80%N.

EXAMPLE 41

1'-(4,4-Diphenylbutyl)-7-fluoro-2-methylspiro[2H-1,4-benzodioxepin-3(5H)4'-piperidine]hydrochloride The compound 7-fluoro-2-methylspiro[2H-1,4-benzodioxepin-3(5H)4'-piperidine]hydrochloride (5 g, 17.39 mmole) was dissolved in 100 ml of DMF and stirred with 5 g of milled, anhydrous potassium carbonate, 15 mg potassium iodide and 4.7 g of 4,4-diphenylbutylchloride (19.13 mmole) at 65° C. under nitrogen, overnight. The reaction, which was determined to be complete by TLC, was cooled, quenched with an equal volume of water and extracted with ether. The ether extracts were combined and backwashed with saturated sodium chloride. The solvent was removed under vacuum. The oily residue was loaded onto a 100 g alumina column packed in either. Fractions of 50 ml were collected and the desired material was found in fraction numbers 2–3. These fractions were combined and the solvent was removed under vacuum. The residual oil was dissolved in anhydrous ether and the hydrochloride salt precipitated. Recrystallization from toluene/ethyl acetate/ethanol afforded 3.0 g (6.05 mmole, 34.79%) of 1'-(4,4-diphenylbutyl)-7-fluoro-2-methylspiro[2H-1,4-benzodioxepin-3(5H)4'-piperidine]hydrochloride, which appeared pure by TLC on silica gel in dichloromethane/methanol (9:1), $R_f=0.6$ and in dichloromethane/2-propanol (1:1), $R_f=0.5$. MS (ci MH+ =460), NMR-DMSO-$d_6$ and IR-KBr were consistent with the structure; m.p.=215°–218° C.

ANALYSIS: Calculated for $C_{30}H_{35}ClFNO_2$: 72.63%C; 7.13%H; 2.82%N; Found: 72.73%C; 6.74%H; 2.56%N.

EXAMPLE 42

1'-[4,4-Bis(4-fluorophenyl)butyl]-7-fluoro-2-methylspiro[2H-1,4-benzodioxepin-3(5H)4'-piperidine]hydrochloride The compound 7-fluoro-2-methylspiro[2H-1,4-benzodioxepin-3(5H)4'-piperidine]hydrochloride (5.0 g, 17.39 mmole) was dissolved in 100 ml of DMF and stirred with 5 g of milled, anhydrous potassium carbonate, 15 mg of potassium iodide and 5.36 g of 4,4-bis(4-fluorophenyl)butylchloride at 65° C. under nitrogen overnight. The reaction, which was determined to be complete by TLC, was cooled, quenched with an equal volume of water and extracted with ether. The ether extracts were combined and backwashed with saturated brine. The solvent was removed under vacuum. The oily residue was loaded onto a 100 g alumina column packed in ether. Fractions of 50 ml were collected and the desired product was found in fraction numbers 2–4. These fractions were combined and the solvent was removed under vacuum. The residual oil was dissolved in anhydrous ether and the hydrochloride salt precipitated. Recrystallization from toluene/ethyl acetate/ethanol afforded 3.9 g (7.34 mole, 42.21%) of 1'[4,4-bis(4-fluorophenyl)butyl]-7-fluoro-2-methylspiro[2H-1,4-benzodioxepin-3(5H)4'-piperidine]hydrochloride, which appeared pure by TLC on silica gel in dichloromethane:methanol (9:1), $R_f=0.6$ and in dichloromethane:2-propanol (1:1), $R_f=0.5$. MS (ci MH+ =496), NMR-DMSO-$d_6$ and IR-KBr were consistent with the structure; m.p.=162°–165° C.

ANALYSIS: Calculated for $C_{30}H_{33}ClF_3NO_2$: 67.72%C; 6.26%H; 2.63%N; Found: 67.35%C; 5.95%H; 2.56%N.

EXAMPLE 43

1'-[2-[Bis(4-fluorophenyl)methoxy]ethyl]-7-fluoro-2-methylspiro[2H-1,4-benzodioxepin-3(5H)4'-piperidine]hydrochloride The compound 7-fluoro-2-methylspiro[2H-1,4-benzodioxepin-3(5H)4'-piperidine]hydrochloride (5 g, 17.4 mmole) was suspended in 100 ml of n-butylacetate along with 5 g of potassium carbonate (milled, anhydrous), 5.4 g of [2-[bis(4-fluorophenyl)methoxy]ethyl chloride (19.1 mmole) and 15 mg of potassium iodide. The mixture was stirred under nitrogen at reflux overnight. The reaction was determined to be complete by TLC. The mixture was filtered and the solvent was removed under vacuum. The residue was loaded onto a 100 g alumina column packed in ether. Fractions of 50 ml of ether were collected and the desired material was found in fraction numbers 3–6. These fractions were combined. The hydrochloride salt was precipitated and dried, resulting in 5.8 g of 1'-[2-[bis(4-fluorophenyl)methoxy]ethyl]-7-fluoro-2-methylspiro[2H-1,4-benzodioxepin-3(5H)4'-piperidine]hydrochloride (10.9 mmole, 62.64%). The material appeared pure by TLC on silica gel in dichloromethane:methanol (9:1), $R_f=0.6$ and in hexane:diethylamine (40:3), $R_f=0.3$. MS (ci MH+ =498), NMR-DMSO-$d_6$ and IR-CHCl$_3$ were consistent with the structure; m.p.=165°–168° C.

ANALYSIS: Calculated for $C_{29}H_{31}ClF_3NO_3$: 65.22%C; 5.86%H; 2.62%N; Found: 65.24%C; 5.81%H; 2.68%N.

EXAMPLE 44

1'-[2-[Bis(4-fluorophenyl)methoxy]ethyl]-2-methylspiro[2H-1,4-benzodioxepin-3(5H)4'-piperidine]hydrochloride The compound 2-methylspiro[2H-1,4-benzodioxepin-3(5H)4'-piperidine]hydrochloride (3.3 g, 12.2 mmole) was suspended in 100 ml of n-butylacetate along with 3 g of potassium carbonate (milled, anhydrous), 3.8 g of 2-[bis(4-fluorophenyl)methoxy]ethyl chloride (13.5 mmole) and 15 mg of potassium iodide. The mixture was stirred under nitrogen and heated at reflux overnight. The reaction was determined to be complete by TLC. The mixture was filtered and the solvent was removed under vacuum. The residue was loaded onto a 100 g alumina column packed in ether. Fractions of 50 ml of ether were collected and the desired material was found in fraction number 3–5. These fractions were combined. The hydrochloride salt was precipitated and was recrystallized from ethyl acetate:2-propanol, yielding 3.3 g of 1'-[2-[bis(4-fluorophenyl)methoxy]ethyl]-2-methylspiro[2H-1,4-benzodioxepin-3(5H)4'-piperidine]hydrochloride (6.4 mmole, 52.5%) in two crops. This material appeared pure by TLC on silica gel in dichloromethane:methanol (9:1) $R_f=0.6$ and in hexane:diethylamine (40:3) $R_f=0.3$. MS (ci MH+ =480), NMR-DMSO-$d_6$ and IR-KBr were consistent with the structure; m.p.=179°–181° C.

ANALYSIS: Calculated for $C_{29}H_{32}ClF_2NO_3$: 67.49%C; 6.26%H; 2.71%N; Found: 67.36%C; 6.23%H; 2.49% N.

What is claimed is:

1. A compound of the formula

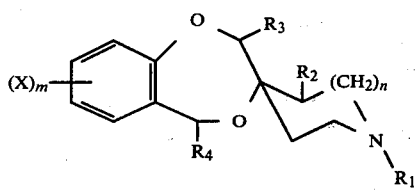

wherein R₁ is a C₃ or C₄ branched or straight chain alkyl or alkenyl group or a C₄-alkynyl group terminally substituted by one or two substituents independently selected from the group consisting of

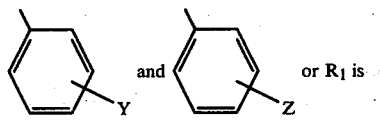 or R₁ is

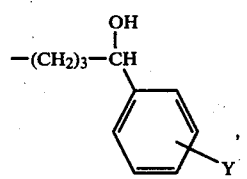,

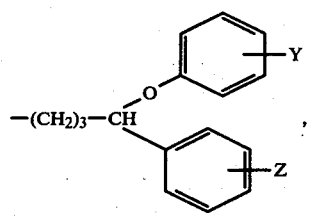,

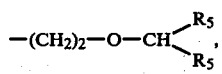,

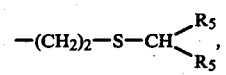,

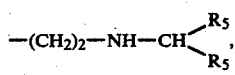,

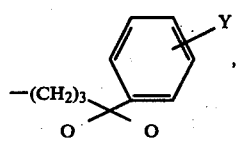,

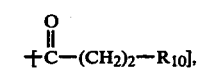,

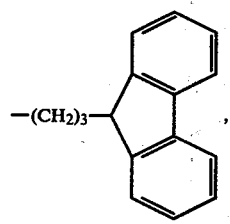,

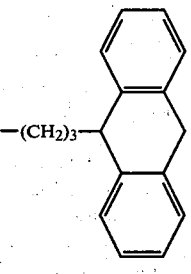, where
Y and Z are the same or different and are independently selected from the group consisting of H, Cl, F, Br, I, —NO₂, —CF₃, C₁ to C₄ straight chain alkyl, alkoxy containing C₁ to C₄ straight chain alkyl, acyl or —NH₂;
each R₅ substituent is independently selected from the group consisting of

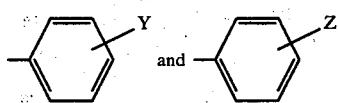;

R₁₀ is 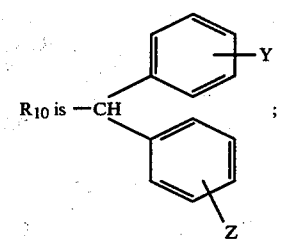;

R₂ is hydrogen when n=0 or R₂ is hydrogen or a C₁ to C₃ straight chain alkyl group when n=1;
R₃ is hydrogen or a C₁ to C₃ straight chain alkyl group;
R₄ is hydrogen or a C₁ to C₃ straight chain alkyl group;
m is zero, 1 or 2;
X is Cl, F, Br, I, —NO₂, —CF₃, —NR₆R₇,

C₁ to C₆ branched or straight chain alkyl, —CN, —O—R₆, —SR₇, —SO₃R₇,

—NHCOR₈, —SO₂R₉ or —SOR₉ where
R₆ is hydrogen or a C₁ to C₆ straight chain alkyl group,
R₇ is hydrogen or a C₁ to C₆ straight chain alkyl group,
R₈ is a C₁ to C₆ branched or straight chain alkyl group,
R₉ is a C₁ to C₆ straight chain alkyl group;
provided that when m=2, the X-substituents can be the same only when X is selected from the group consisting of Cl, F, Br, I, $C_1$ to $C_6$ branched or straight chain alkyl or $-O-R_6$;

n is zero or 1;

and the pharmaceutically acceptable salts and optical and geometric isomers thereof.

2. A compound according to claim 1 in which $R_1$ is a $C_4$ branched or straight chain alkyl or alkenyl group terminally substituted by p-fluorophenyl, bis-phenyl, bis-p-chlorophenyl or bis-p-fluorophenyl groups; or $R_1$ is

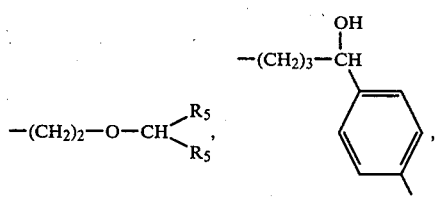

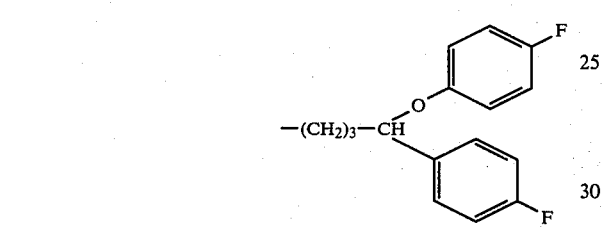

where $R_5$ is a phenyl or p-fluorophenyl group.

3. A compound according to claim 2 in which $R_2$, $R_3$ and $R_4$ are independently selected from hydrogen and a $C_1$ to $C_3$ straight chain alkyl groups.

4. A compound according to claim 1 in which m=0.

5. A compound according to claim 1 in which m=1.

6. A compound according to claim 1 in which m=2.

7. A compound according to claim 5 in which X is Cl, F or Br.

8. A compound of the formula

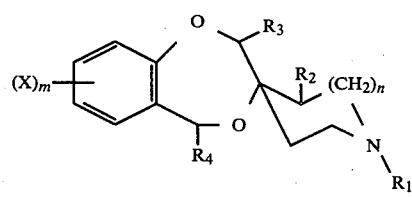

wherein $R_1$ is a $C_4$ branched or straight chain alkyl or alkenyl group terminally substituted by p-fluorophenyl, bis-phenyl or bis-p-fluorophenyl groups; or $R_1$ is

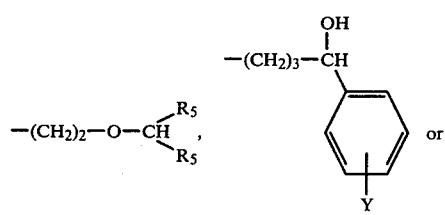 or

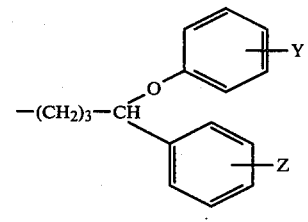

where Y and Z are the same or different and are independently selected from the group consisting of H, Cl, F, Br, I, $-NO_2$, $-CF_3$, $C_1$ to $C_4$ straight chain alkyl, alkoxy containing $C_1$ to $C_4$ straight chain alkyl, acyl or $-NH_2$;

each $R_5$ substituent is independently selected from the group consisting of

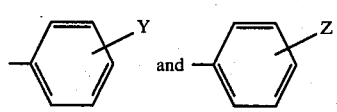

$R_2$, $R_3$ and $R_4$ are independently selected from hydrogen and methyl;

X is Cl, F Br, I, $-NO_2$, $-CH_3$ or $-OCH_3$;

m is zero, 1 or 2;

n is zero or 1;

provided that when m=2, the X-substituents can be the same only when X is selected from the group consisting of Cl, F, Br, I, $-CH_3$ and $-OCH_3$; and the pharmaceutically acceptable salts and optical and geometric isomers thereof.

9. A compound according to claim 8 in which n=1.

10. A compound according to claim 9 in which $R_2$ and $R_4$ are each hydrogen.

11. A compound according to claim 10 in which X is Cl, F or Br.

12. A compound according to claim 11 in which $R_3$ is $-CH_3$.

13. A compound according to claim 12 which is 1'-[4-(4-fluorophenyl)butyl]-2-methylspiro[2H-1,4-benzodioxepin-2(5H)4'-piperidine].

14. A compound according to claim 12 which is 7-chloro-2-methyl-1'-(3,3-diphenylpropyl)spiro[2H-1,4-benzodioxepin-3(5H)4'-piperidine].

15. A compound according to claim 12 which is 1'-[4-(4-fluorophenoxy)-4-(4-fluorophenyl)butyl]-2-methylspiro[2H-1,4-benzodioxepin-3(5H)4'-piperidine].

16. A compound according to claim 12 which is 1'-[4,4-bis(4-chlorophenyl)butyl]-2-methylspiro[2H-1,4-benzodioxepin-3(5H)4'-piperidine].

17. A compound of the formula

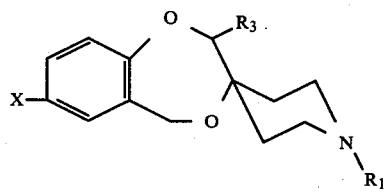

-continued

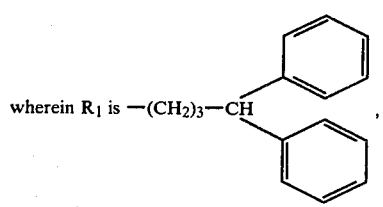
wherein R₁ is —(CH₂)₃—CH

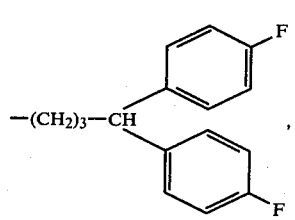
—(CH₂)₃—CH

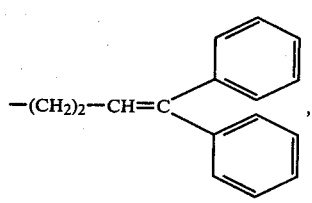
—(CH₂)₂—CH=C

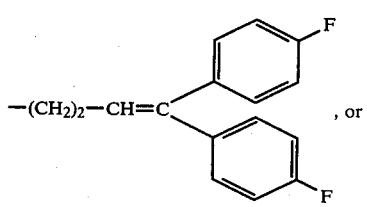
—(CH₂)₂—CH=C , or

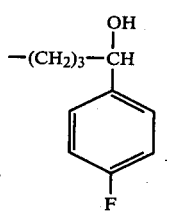
—(CH₂)₃—CH ;

R₃ is H or —CH₃;
X is Cl, F or Br;
and the pharmaceutically acceptable salts and optical and geometric isomers thereof.

18. A compound according to claim 17 which is 1'-[4,4-bis-(4-fluorophenyl)butyl]-2-methylspiro[2H-1,4-benzodioxepin-3(5H)4'-piperidine].

19. A compound according to claim 17 which is 1'-[4,4-bis-(4-fluorophenyl)-3-butenyl]-2-methylspiro[2H-1,4-benzodioxepin-3(5H)4'-piperidine].

20. A compound according to claim 17 which is 1'-(4,4-diphenylbutyl)-2-methylspiro[2H-1,4-benzodioxepin-3(5H)4'-piperidine].

21. A compound according to claim 17 which is 1'-[4,4-diphenyl-3-butenyl]-2-methylspiro[2H-1,4-benzodioxepin-3(5H)4'-piperidine].

22. A compound according to claim 17 which is 1'-[4,4-diphenyl-3-butenyl]-7-chloro-2-methylspiro[2H-1,4-benzodioxepin-3(5H)4'-piperidine].

23. A compound according to claim 17 which is 1'-[4,4-diphenylbutyl]-7-chloro-2-methylspiro[2H-1,4-benzodioxepin-3(5H)4'-piperidine].

24. A compound according to claim 17 which is 1'-[4-hydroxy-4-(4-fluorophenyl)butyl]-2-methylspiro-[2H-1,4-benzodioxepin-3(5H)4'-piperidine].

25. A compound according to claim 17 which is 7-bromo-1'-[4,4-bis(4-fluorophenyl)butyl]-2-methylspiro-[2H-1,4-benzodioxepin-3(5H)4'-piperidine].

26. A compound according to claim 17 which is 1'-(4,4-diphenylbutyl)-7-fluoro-2-methylspiro[2H-1,4-benzodioxepin-3(5H)4'piperidine].

27. A compound according to claim 17 which is 1'-[4,4-bis(4-fluorophenyl)butyl]-7-fluoro-2-methylspiro[2H-1,4-benzodioxepin-3(5H)4'-piperidine].

28. A method for reducing hypertension in a mammal by administering to a mammal, in an amount sufficient to reduce blood pressure in the mammal, a compound of the formula

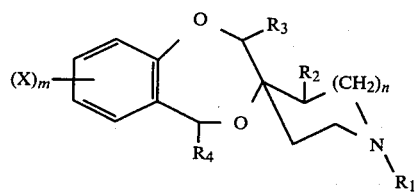

wherein R₁ is a C₃ or C₄ branched or straght chain alkyl or alkenyl group or a C₄-alkynyl group terminally substituted by one or two substituents independently selected from the group consisting of

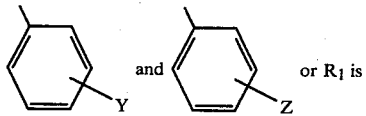
and                or R₁ is

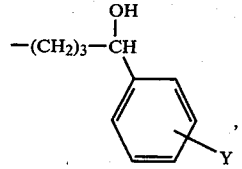

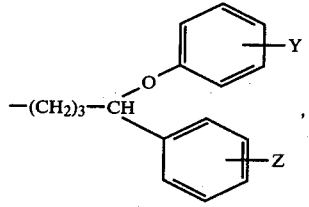

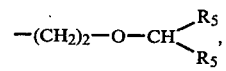
—(CH₂)₂—O—CH(R₅)(R₅),

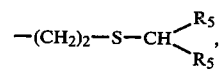
—(CH₂)₂—S—CH(R₅)(R₅),

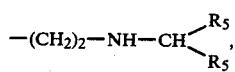
—(CH₂)₂—NH—CH(R₅)(R₅),

UNITED STATES PATENT AND TRADEMARK OFFICE
CERTIFICATE OF CORRECTION

PATENT NO. : 4,405,631

DATED : September 20, 1983

INVENTOR(S) : Raymond W. Kosley, Jr. et al.

It is certified that error appears in the above—identified patent and that said Letters Patent is hereby corrected as shown below:

Column 12, line 33: Compound 22 - "CH$_2$  ...

Should be: 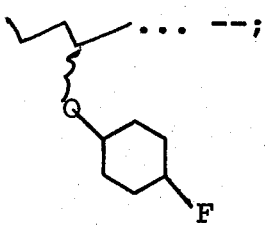 ";

Column 20, line 48: "$C_{24}H_{31}ClFNO_2$:"

Should be: --$C_{24}H_{31}ClFNO_2$:--;

Column 28, line 48: "(+7)" should be --(7)--;

Column 30, line 25: "...-methylspiro[B..."

Should be: --...-methylspiro[2H-....--;

-continued

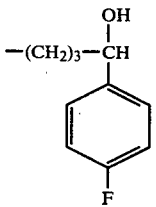

$R_3$ is —$CH_3$;

X is H, Cl, F or Br;

or a pharmaceutically acceptable salts and optical and geometric isomers thereof.

45. A method according to claim 44 in which the compound is 1'-[4,4-bis-(4-fluorophenyl)butyl]-2-methylspiro[2H-1,4-benzodioxepin-3(5H)4'-piperidine].

46. A method according to claim 44 in which the compound is 1'-[4,4-bis-(4-fluorophenyl)-3-butenyl]-2-methylspiro[2H-1,4-benzodioxepin-3(5H)4'-piperidine].

47. A method according to claim 44 in which the compound is 1'-(4,4-diphenylbutyl)-2-methylspiro[2H-1,4-benzodioxepin-3(5H)4'-piperidine].

48. A method according to claim 44 in which the compound is 1'-[4,4-diphenyl-3-butenyl]-2-methylspiro[2H-1,4-benzodioxepin-3(5H)4'-piperidine].

49. A method according to claim 44 in which the compound is 1'-[4,4-diphenyl-3-butenyl]-7-chloro-2-methylspiro[2H-1,4-benzodioxepin-3(5H)4'-piperidine].

50. A method according to claim 44 in which the compound is 1'-[4,4-diphenylbutyl]-7-chloro-2-methylspiro[2H-1,4-benzodioxepin-3(5H)4'-piperidine].

51. A method according to claim 44 in which the compound is 1'-[4-hydroxy-4-(4-fluorophenyl)butyl]-2-methylspiro[2H-1,4-benzodioxepin-3(5H)4'-piperidine].

52. A method according to claim 44 in which the compound is 7-bromo-1'-[4,4-bis(4-fluorophenyl)butyl]-2-methylspiro[2H-1,4-benzodioxepin-3(5H)4'-piperidine].

53. A method according to claim 44 in which the compound is 1'-(4,4-diphenylbutyl)-7-fluoro-2-methylspiro[2H-1,4-benzodioxepin-3(5H)4'-piperidine].

54. A method according to claim 44 in which the compound is 1'-[4,4-bis(4-fluorophenyl)butyl]-7-fluoro-2-methylspiro[2H-1,4-benzodioxepin-3(5H)4'-piperidine].

55. A pharmaceutical composition comprising a compound according to any one of claims 1 to 27 and a pharmaceutically acceptable carrier thereof.

* * * * *

UNITED STATES PATENT AND TRADEMARK OFFICE
CERTIFICATE OF CORRECTION

PATENT NO. : 4,405,631

DATED : September 20, 1983

INVENTOR(S) : Raymond W. Kosley, Jr. et al.

It is certified that error appears in the above—identified patent and that said Letters Patent is hereby corrected as shown below:

Column 12, line 33: Compound 22 - "CH$_2$  ...

Should be: --CH$_2$ ... --; 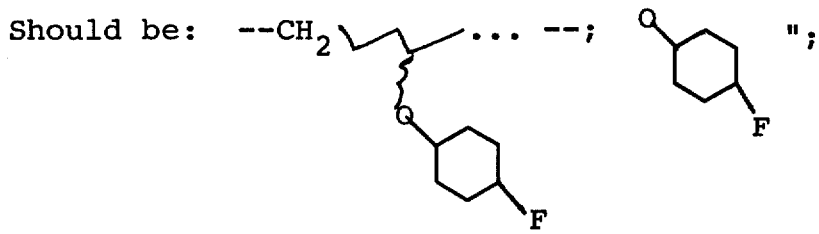 ";

Column 20, line 48: "C$_{24}$H$_{31}$CLFNO$_2$:"

Should be: --C$_{24}$H$_{31}$ClFNO$_2$:--;

Column 28, line 48: "(+7)" should be --(7)--;

Column 30, line 25: "...-methylspiro[B..."

Should be: --...-methylspiro[2H-...--;

UNITED STATES PATENT AND TRADEMARK OFFICE
CERTIFICATE OF CORRECTION

PATENT NO. : 4,405,631

DATED : September 20, 1983

INVENTOR(S) : Raymond W. Kosley, Jr. et al.

It is certified that error appears in the above—identified patent and that said Letters Patent is hereby corrected as shown below:

Column 32, line 43: "...tert-butoxide..."

Should be: --...tert-butoxide...--;

Column 32, line 45: "...tert-butoxide..."

Should be: --...tert-butoxide...--.

Signed and Sealed this

Twenty-first Day of February 1984

[SEAL]

Attest:

GERALD J. MOSSINGHOFF

Attesting Officer     Commissioner of Patents and Trademarks